United States Patent
Wei et al.

(10) Patent No.: US 11,883,552 B2
(45) Date of Patent: Jan. 30, 2024

(54) METHOD FOR CONTROLLING HYGIENE OF A PORTABLE PACKAGED FOOD CONTAINER

(71) Applicant: Ecolab USA Inc., Saint Paul, MN (US)

(72) Inventors: Wenbin Wei, Shanghai (CN); Ying Zhang, Shanghai (CN); Zhili Ding, Shanghai (CN); Huarong Yu, Shanghai (CN)

(73) Assignee: ECOLAB USA INC., Saint Paul, MN (US)

( * ) Notice: Subject to any disclaimer, the term of this patent is extended or adjusted under 35 U.S.C. 154(b) by 0 days.

(21) Appl. No.: 16/349,454

(22) PCT Filed: Feb. 19, 2019

(86) PCT No.: PCT/CN2019/075440
§ 371 (c)(1),
(2) Date: May 13, 2019

(87) PCT Pub. No.: WO2019/214310
PCT Pub. Date: Nov. 14, 2019

(65) Prior Publication Data
US 2020/0261612 A1 Aug. 20, 2020

(30) Foreign Application Priority Data

May 11, 2018 (WO) ................ PCT/CN2018/086468
Nov. 7, 2018 (WO) ................ PCT/CN2018/114274

(51) Int. Cl.
*A61L 2/22* (2006.01)
*A61L 2/16* (2006.01)
(Continued)

(52) U.S. Cl.
CPC .................. *A61L 2/22* (2013.01); *A61L 2/16* (2013.01); *A61L 2/24* (2013.01); *B08B 9/00* (2013.01);
(Continued)

(58) Field of Classification Search
CPC ............ A61L 2202/14; A61L 2202/15; A61L 2202/16; A61L 2202/17; A61L 2202/23;
(Continued)

(56) References Cited

U.S. PATENT DOCUMENTS 6,189,330 B1   2/2001  Retallick et al.
6,445,976 B1   9/2002  Ostro
(Continued)

FOREIGN PATENT DOCUMENTS

CN      1559869 A       1/2005
CN      101185765 A     5/2008
(Continued)

OTHER PUBLICATIONS

Machine translation of CN104867246A (Year: 2015).*
(Continued)

*Primary Examiner* — Douglas Lee
(74) *Attorney, Agent, or Firm* — Schwegman Lundberg & Woessner, P.A.

(57) ABSTRACT

A method is provided for operating a system to automatically conduct hygiene cycles for a confined space such an interior space of a box suitable for storing and/or carrying packaged food. The system may include a hygiene device that can be attached to the box to conduct the hygiene cycles and a mobile device that can wirelessly communicate with the hygiene device to control the conduction of the hygiene cycles. The method may include automatically collecting information related to the hygiene cycles using the hygiene device and transmitting the collected information to a network directly or through the mobile device.

20 Claims, 17 Drawing Sheets

(51) Int. Cl.

| | | |
|---|---|---|
| *A61L 2/24* | (2006.01) | |
| *B08B 9/00* | (2006.01) | |
| *B08B 9/08* | (2006.01) | |
| *B08B 9/093* | (2006.01) | |
| *B08B 13/00* | (2006.01) | |
| *B65B 55/02* | (2006.01) | |
| *A61L 12/08* | (2006.01) | |
| *B65B 55/04* | (2006.01) | |
| *B65B 55/10* | (2006.01) | |
| *B65D 81/24* | (2006.01) | |
| *G08B 5/22* | (2006.01) | |
| *H01L 21/67* | (2006.01) | |

(52) U.S. Cl.
CPC .............. *B08B 9/08* (2013.01); *B08B 9/0861* (2013.01); *B08B 9/093* (2013.01); *B08B 13/00* (2013.01); *B65B 55/02* (2013.01); *B65B 55/04* (2013.01); *B65B 55/10* (2013.01); *B65D 81/24* (2013.01); *G08B 5/223* (2013.01); *A61L 12/086* (2013.01); *A61L 2202/14* (2013.01); *A61L 2202/15* (2013.01); *A61L 2202/16* (2013.01); *A61L 2202/17* (2013.01); *A61L 2202/23* (2013.01); *B08B 2209/08* (2013.01); *H01L 21/6704* (2013.01); *H01L 21/67028* (2013.01)

(58) Field of Classification Search
CPC . A61L 2/22; A61L 2/24; A61L 12/086; A61L 2/16; B08B 13/00; B08B 9/00; B08B 9/0861; B08B 9/093; B08B 2209/08; B08B 9/08; B65B 55/02; B65B 55/04; B65B 55/10; G08B 5/223; G08B 21/24; A47J 43/00; B65D 81/24; G08C 17/02; H01L 21/67028; H01L 21/6704
See application file for complete search history.

(56) References Cited

U.S. PATENT DOCUMENTS

| | | | |
|---|---|---|---|
| 6,550,487 | B1 | 4/2003 | Duckett et al. |
| 7,021,323 | B1 | 4/2006 | Ishikawa et al. |
| 9,595,461 | B2 | 3/2017 | Takahara et al. |
| 11,285,231 | B2 | 3/2022 | Wei et al. |
| 2002/0003148 | A1 | 1/2002 | Gibson |
| 2002/0134800 | A1 | 9/2002 | Johnson et al. |
| 2004/0118291 | A1 | 6/2004 | Carhuff et al. |
| 2006/0150829 | A1 | 7/2006 | Cheung |
| 2006/0276768 | A1 | 12/2006 | Miller et al. |
| 2008/0152537 | A1 | 6/2008 | Wild et al. |
| 2009/0138107 | A1* | 5/2009 | Ha .................. D06F 34/05 700/90 |
| 2011/0162681 | A1 | 7/2011 | Mulleris |
| 2011/0197464 | A1* | 8/2011 | Chappell ............ F26B 9/003 34/232 |
| 2011/0197921 | A1 | 8/2011 | Rubin et al. |
| 2012/0174795 | A1 | 7/2012 | Uspenski et al. |
| 2012/0241537 | A1 | 9/2012 | Schwei et al. |
| 2012/0251385 | A1 | 10/2012 | Hsieh |
| 2015/0374868 | A1 | 12/2015 | Bruce et al. |
| 2016/0107816 | A1 | 4/2016 | Larpenteur et al. |
| 2017/0069199 | A1 | 3/2017 | Magno et al. |
| 2017/0252472 | A1* | 9/2017 | Dang .................. H04W 76/11 |
| 2017/0286904 | A1 | 10/2017 | Paris, Jr. et al. |
| 2017/0320054 | A1 | 11/2017 | Crum et al. |
| 2018/0078330 | A1 | 3/2018 | Russ |
| 2018/0142394 | A1* | 5/2018 | DeBates ............ G06K 7/10366 |
| 2018/0154028 | A1* | 6/2018 | Offutt ..................... A61L 2/24 |
| 2018/0184839 | A1 | 7/2018 | Vetterli et al. |
| 2018/0236117 | A1* | 8/2018 | Agmont E Silva ....... B08B 9/08 |

FOREIGN PATENT DOCUMENTS

| | | |
|---|---|---|
| CN | 101208568 A | 6/2008 |
| CN | 203279755 | 11/2013 |
| CN | 103612828 A | 3/2014 |
| CN | 103635207 | 3/2014 |
| CN | 104144752 A | 11/2014 |
| CN | 104249896 A | 12/2014 |
| CN | 104867246 A * | 8/2015 |
| CN | 104867246 A | 8/2015 |
| CN | 204854123 U | 12/2015 |
| CN | 105242657 A | 1/2016 |
| CN | 105383800 A | 3/2016 |
| CN | 106575426 A | 4/2017 |
| CN | 106715274 A | 5/2017 |
| CN | 206172223 U | 5/2017 |
| CN | 107187700 | 9/2017 |
| CN | 206456776 U | 9/2017 |
| CN | 107845206 A | 3/2018 |
| CN | 207197042 U | 4/2018 |
| CN | 207258372 A | 4/2018 |
| CN | 207258372 U | 4/2018 |
| CN | 207258372 U * | 4/2018 |
| DE | 19958290 A1 | 6/2000 |
| FR | 2934991 A1 | 2/2010 |
| GB | 2123110 A | 1/1984 |
| JP | H08192125 A | 7/1996 |
| JP | 2001315721 A | 11/2001 |
| JP | 2016-141427 A | 8/2016 |
| KR | 100838949 B1 | 6/2008 |
| KR | 2009-0041003 A | 4/2009 |
| KR | 20210005171 A | 1/2021 |
| WO | WO-2016/113235 A1 | 7/2016 |

OTHER PUBLICATIONS

Machine translation of CN207258372U (Year: 2018).*
U.S. Appl. No. 16/349,413 U.S. Pat. No. 10,758,638, filed May 13, 2019, Hygiene System for a Portable Packaged Food Container.
U.S. Appl. No. 16/941,285, filed Jul. 28, 2020, Hygiene System for a Portable Packaged Food Container.
"International Application Serial No. PCT/CN2018/086468, International Search Report dated Feb. 11, 2019", 5 pgs.
"International Application Serial No. PCT/CN2018/086468, Written Opinion dated Feb. 11, 2019", 4 pgs.
"International Application Serial No. PCT/CN2018/114274, International Search Report dated Feb. 15, 2019", 4 pgs.
"International Application Serial No. PCT/CN2018/114274, Written Opinion dated Feb. 15, 2019", 4 pgs.
"International Application Serial No. PCT/CN2019/075440, International Search Report dated Apr. 25, 2019", 4 pgs.
"International Application Serial No. PCT/CN2019/075440, Written Opinion dated Apr. 25, 2019", 4 pgs.
"U.S. Appl. No. 16/941,285, Non Final Office Action dated Jul. 14, 2021", 13 pgs.
"European Application Serial No. 19798975.9, Response Filed Jun. 25, 2021 to Communication pursuant to Rules 161(2) and 162 EPC", 13 pgs.
"U.S. Appl. No. 16/941,285, Response filed Oct. 13, 2021 to Non Final Office Action dated Jul. 14, 2021", 9 pages.
"U.S. Appl. No. 16/941,285, Notice of Allowance dated Nov. 23, 2021", 8 pages.
"Chinese Application Serial No. 201980000626.3, Office Action dated Nov. 22, 2021", with English translation, 27 pages.
"Indian Application Serial No. 202017051624, First Examination Report dated Jan. 21, 2022", 6 pgs.
"U.S. Appl. No. 16/941,285, Corrected Notice of Allowability dated Feb. 18, 2022", 2 pgs.
"Chinese Application Serial No. 201880004352.0, Office Action dated Feb. 9, 2022", (w/ English Translation), 23 pages.
"Chinese Application Serial No. 201880004352.0, Response filed Jun. 8, 2022 to Office Action dated Feb. 9, 2022", (w/ English Translation of Claims), 18 pgs.
"Chinese Application Serial No. 201980000626.3, Office Action dated Apr. 22, 2022", (w/ English Translation), 29 pgs.

(56) References Cited

OTHER PUBLICATIONS

"Chinese Application Serial No. 201980000626.3, Response Filed Mar. 18, 2022 to Office Action dated Nov. 22, 2021", (w/ English Translation of Claims), 28 pages.

"Chinese Application Serial No. 201980000626.3, Response filed Jun. 21, 2022 to Office Action dated Apr. 22, 2022", (w/ English Translation of Claims), 23 pgs.

"European Application Serial No. 19798975.9, Extended European Search Report dated Mar. 7, 2022", 10 pgs.

"Korean Application Serial No. 10-2020-7034033, Notice of Preliminary Rejection dated Jun. 17, 2022", (w/ English Translation), 17 pgs.

"Singaporean Application Serial No. 11202011142Y, Written Opinion dated Apr. 1, 2022", 4 pgs.

U.S. Appl. No. 17/656,566, filed Mar. 25, 2022, Hygiene System for a Portable Packaged Food Container.

"Chinese Application Serial No. 201880004352.0, Office Action dated Aug. 16, 2022", (w/ English Translation), 25 pgs.

"Chinese Application Serial No. 201880004352.0, Response filed Oct. 14, 2022 to Office Action dated Aug. 16, 2022", (w/ English Translation of Claims), 18 pgs.

"Chinese Application Serial No. 201980000626.3, Office Action dated Aug. 8, 2022", (w/ English Translation), 31 pgs.

"Chinese Application Serial No. 201980000626.3, Response filed Oct. 21, 2022 to Office Action dated Nov. 22, 2021", w/o English claims, 4 pgs.

"European Application Serial No. 19798975.9, Response filed Sep. 13, 2022 to Extended European Search Report dated Mar. 7, 2022", 15 pgs.

"Indian Application Serial No. 202017051624, Response filed Jul. 21, 2022 to First Examination Report dated Jan. 21, 2022", 218 pgs.

"Indonesia Application Serial No. P00202008822, Office Action dated Oct. 3, 2022", w/ English translation, 4 pgs.

"Korean Application Serial No. 10-2020-7034033, Notice of Preliminary Rejection dated Nov. 10, 2022", W/O English Translation, 3 pgs.

Zuo, Chunkuan, et al., "Marine Power Plant", (Jun. 30, 2012), 8 pgs.

"U.S. Appl. No. 17/656,566, Non-Final Office Action dated Apr. 24, 2023", 18 pgs.

"Chinese Application Serial No. 201880004352.0, Notification to Grant dated Dec. 5, 2022", (w/ English Translation), 9 pgs.

"Chinese Application Serial No. 201980000626.3, Decision of Rejection dated Dec. 9, 2022", (w/ English Translation), 16 pgs.

"Chinese Application Serial No. 201980000626.3, Response filed Feb. 28, 2023 to Decision of Rejection dated Dec. 9, 2022", (w/ English Translation of Claims), 62 pgs.

"Korean Application Serial No. 10-2020-7034033, Notice to Grant dated Mar. 22, 2023", (w/ English Translation), 4 pgs.

"Korean Application Serial No. 10-2020-7034033, Response filed Dec. 26, 2022 to Notice of Preliminary Rejection dated Nov. 10, 2022", (w/ English Translation of Claims), 9 pgs.

Liu, C. J., et al., "Development and Application of a "Foreign Device" Module in IMS of the Sterilization and Supply Center", (Abstract), China Medical Devices, No. 2, (Feb. 25, 2015), 1 pg.

* cited by examiner

METHOD FOR CONTROLLING HYGIENE OF A PORTABLE PACKAGED FOOD CONTAINER

CROSS REFERENCE TO RELATED APPLICATIONS

This application is a U.S. National Stage Filing under 35 U.S.C. 371 from International Application No. PCT/CN2019/075440, filed on Feb. 19, 2019, which claims priority to International Patent Application No. PCT/CN2018/114274, entitled "HYGIENE SYSTEM FOR A PORTABLE PACKAGED FOOD CONTAINER", filed on Nov. 7, 2018 and International Patent Application No. PCT/CN2018/086468, entitled "HYGIENE SYSTEM FOR A PORTABLE PACKAGED FOOD CONTAINER", filed on May 11, 2018, the contents of which are incorporated herein by reference in their entireties.

TECHNICAL FIELD

This document relates generally to device hygiene and more particularly to a method and apparatus for conducting automatic cleaning and/or sanitization cycles for a confined space such as interior of a box for containing packaged food.

BACKGROUND

Small and confined spaces, such as the interior of a food delivery box, are difficult to clean and/or sanitize. For example, boxes used to deliver ready-to-eat foods, such as ordered by a customer from a restaurant, need periodic cleaning and sanitization to ensure food hygiene. This may be done by manually spraying a chemical agent onto surfaces of each delivery box. Quality and thoroughness of such manual cleaning and/or sanitization depend on the person performing the procedure, and are inconsistent because, for example, there is no mechanism ensuring that the entire surfaces are covered and/or in a substantially uniform fashion. A two-step cleaning and sanitizing procedure makes each cycle even more complicated and less consistent. Additionally, a manual operation does not provide an objective record showing that a hygiene procedure is routinely followed.

SUMMARY

A system may automatically conduct hygiene cycles for a confined space such an interior space of a box suitable for storing and/or carrying packaged food. The system may include a hygiene device that can be attached to the box to conduct the hygiene cycles and a user interface device that can wirelessly communicate with the hygiene device to control the conduction of the hygiene cycles. The system may also automatically collect information related to the hygiene cycles using the hygiene device and transmit the collected information to a network directly or through the user interface device.

An example of a system for cleaning and sanitizing a box configured to be carried by a user may include a hygiene device. The hygiene device may be configured to be attached to the box, and may include an agent container configured to contain a hygiene agent, a spray nozzle configured to be inserted into the box (or otherwise placed in the box to perform its function), a pump in fluid communication with the agent container and in fluid communication with the spray nozzle, and a control circuit. The pump may be configured to pump the hygiene agent through the spray nozzle to produce a mist of the hygiene agent in the box. The control circuit may be configured to control hygiene cycles and may include a communication circuit configured to transmit and receive information, a hygiene cycle management circuit configured to initiate each cycle of the hygiene cycles, and a monitoring circuit configured to record information related to performance of each cycle of the hygiene cycles and to transmit the recorded information out of the hygiene device through the communication circuit.

An example of a method for cleaning and sanitizing a box configured to be carried by a user is also provided. The method may include verifying emptiness of the box, starting an automatic hygiene cycle using a battery-powered portable hygiene device attached to the box, recording information related to performance of the hygiene cycle, and transmitting the recorded information to an analysis center for analysis and monitoring of hygiene status of the box.

Another example of a system for cleaning and sanitizing a box configured to be carried by a user may include a hygiene device and a user interface device. The hygiene device may be configured to be affixed to the box, to conduct hygiene cycles each including spray of a hygiene agent into the box, to record information related to performance of each cycle of the hygiene cycles, and to transmit the recorded information out of the hygiene device via a wireless communication link. The user interface device may be configured to transmit commands controlling the conduction of the hygiene cycles to the hygiene device via the wireless communication link and to receive the recorded information transmitted from the hygiene device via the wireless communication link.

Another example of a method for cleaning and sanitizing a box configured to be carried by a user is also provided. The method may include conducting hygiene cycles using a hygiene device affixed onto the box, controlling the conduction of each hygiene cycle of the hygiene cycles using a user interface device configured to be carried by the user and to be communicatively coupled to the hygiene device via a wireless communication link, recording information related to performance of each hygiene cycle of the hygiene cycles using the hygiene device, and transmitting the recorded information from the hygiene device to the user interface device.

An example of a system for controlling a hygiene device may include a mobile device. The hygiene device may be configured to be affixed to a food delivery box to conduct hygiene cycles each including spray of a hygiene agent into the box and to record information related to performance of the hygiene cycles. The hygiene device may be provided to a user of the box by a provider having a provider's network. The mobile device may be configured to be communicatively coupled to the hygiene device via a first wireless communication link, to transmit commands controlling the conduction of the hygiene cycles to the hygiene device via the first wireless communication link, and to receive the recorded information transmitted from the hygiene device via the first wireless communication link.

An example of a non-transitory machine-readable medium may include instructions, which when executed by a machine, cause the machine to perform a method for controlling a hygiene device. The hygiene device may be affixed to a food delivery box and configured to conduct hygiene cycles each including spray of a hygiene agent into the box and to record information related to performance of the hygiene cycles. The method may include transmitting a cycle start command to the hygiene device via a first wireless communication link and receiving the recorded information from the hygiene device via the first wireless communications link. The cycle start command is to start a hygiene cycle of the hygiene cycles. The recorded information may include at least one of a spray status of the started hygiene cycle, a device identification identifying the box, a time stamp of the started hygiene cycle, a pumping time during which the hygiene agent is pumped to spray, a battery level of the hygiene device, or a lid open alarm indicating that a lid of the hygiene device is open.

This summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
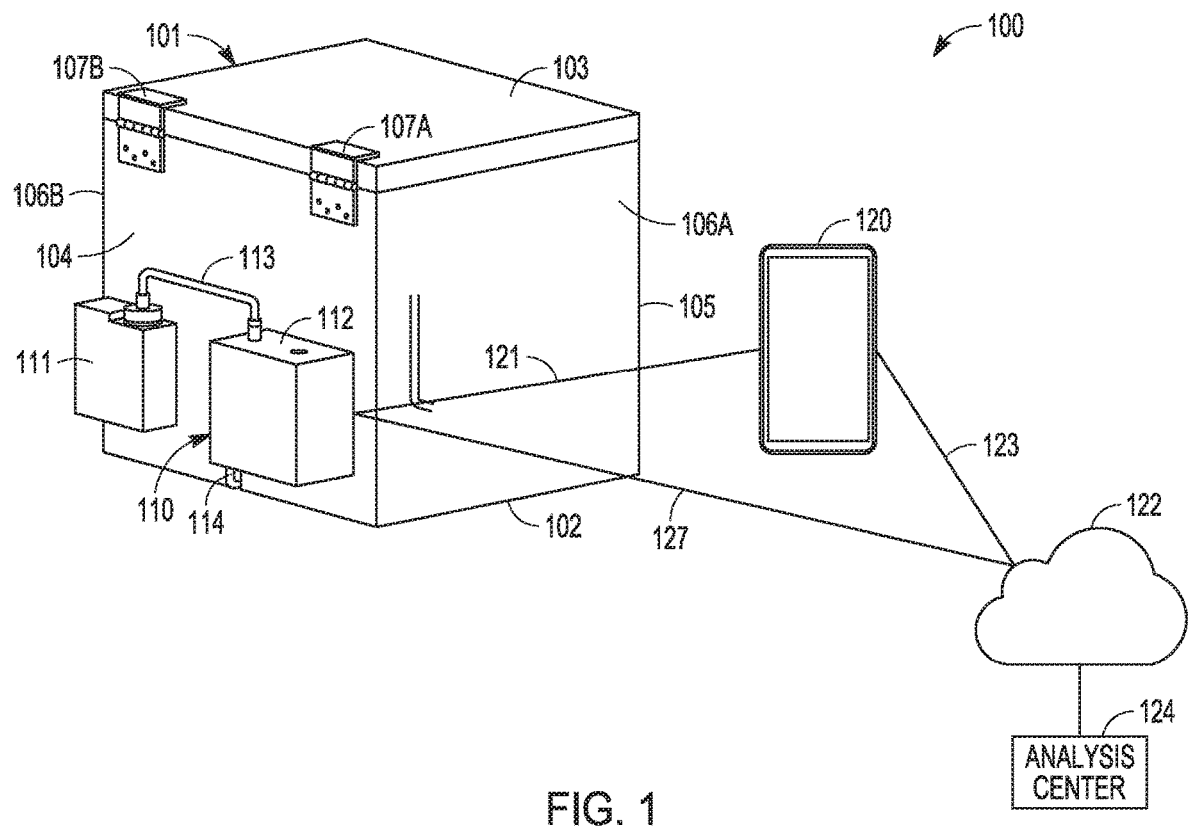
FIG. 1 is a block diagram illustrating an embodiment of a system for cleaning and sanitizing a box.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present invention is defined by the appended claims, along with the full scope of legal equivalents to which such claims are entitled.

This document discusses, among other things, a system for automatically conducting hygiene cycles for a confined space and automatically logging the hygiene cycles. The system can be constructed as a portable clean-in-place ("CIP") system. The hygiene cycle log can include various information collected by the system and can be transmitted to an analysis center through a telecommunication network.

In this document, "hygiene" can include cleaning, sanitization, or cleaning and sanitization (C&S). For example, a "hygiene agent" can include a cleaning agent, a sanitization agent, or a cleaning and sanitization (C&S) agent; a "hygiene cycle" can include a cleaning cycle, a sanitization cycle, or a cleaning and sanitization (C&S) cycle; and a "hygiene procedure" can include a cleaning procedure, a sanitization procedure, or a cleaning and sanitization (C&S) procedure.

An example of the confined space includes the confined space in a closed box for carrying or storing packaged ready-to-eat foods. An example of such a box includes a food delivery box for carrying cooked foods from a kitchen to a dinning place in a location remote from the kitchen. A hygiene procedure for such a box may be established to ensure food safety (e.g., according to pertinent regulatory requirements). When the procedure is carried out manually, compliance is difficult to ensure, and no objective evidence of compliance is recorded.

The present system provides an intelligent system that can spray a hygiene agent onto surfaces of a confined space with a substantially uniform distribution under automatic control for conducting hygiene cycles periodically or according to other specified schedule and/or criteria. In some embodiments, a 2-in-1 hygiene agent (also referred to as a C&S agent) combines cleaning and sanitation into an efficient single step. In various embodiments, the hygiene agent can include surfactant as cleaning agent. In various embodiments, the hygiene agent can include peroxide, quaternary ammonium salt (QUAT), and/or chlorine based sanitizers. Soft water agent can be used to protect equipment and prolong lifespan of the hygiene system. The present system also collects hygiene cycle information automatically and transmits the collected information to one or more designated receiving locations for analysis and monitoring.

Existing hygiene systems that are intended for large spaces and need much power to operate, plenty of water to flush, and compress air to dry are not suitable for small spaces such as the food delivery box, which can be small enough, for example, to be carried by hand and/or by an electric moped or motorcycle. The present system can be battery-powered and portable, such as a system that can be easily attached to the food delivery box to perform controlled spray of the hygiene agent onto interior surfaces of the food delivery box when it is empty. In one embodiment, the present system uses a single spray nozzle configured to function with a diaphragm pump to spray the hygiene agent with nebulization to ensure that the hygiene agent covers all surfaces of a confined space, such as the cavity of a rectangular box having six planar surfaces.

In various embodiments, the present system can include a control system that receives a command and initiates a hygiene cycle in response to the command. The command can be received by the system from a remote device via a communication link. In response to the hygiene cycle being initiated, an electronic circuit of the present system generates a signal to start the diaphragm pump to spray, resulting in a substantially uniform distribution of the hygiene agent on all the surfaces of the confine space. The electronic circuit can control automatic conduction of the hygiene cycle, record time of the hygiene cycle and/or other hygiene cycle information, and send the recorded information including the time to the analysis center.

In various embodiments, the hygiene agent can include one or more chemical substances in liquid form. An example of the hygiene agent includes a cleaning agent, a sanitization agent, or a 2-in-1 C&S agent selected such that when being sprayed into a confined space using the present system, the quantity of the agent distributed on surfaces of the confined space can produce a result that satisfies pertinent regulatory requirements for cleaning and sanitizing efficacy. This quantity of agent distribution can be achieved by configuring the spray nozzle and diaphragm pump to provide for chemical nebulization and determining a duration of spraying for each hygiene cycle. In various embodiments, the duration of spraying can be determined, and precisely controlled, to provide the required cleaning and sanitizing efficacy while avoiding excessive use of the hygiene agent that may cause undesirable effects such as chemical odor.

While a hygiene system for the food delivery box is specifically discussed in this document as an example, the present subject matter is not limited to such an application but can be used to apply liquid and/or gas into any confined space, for purposes including but not limited to cleaning and sanitizing the confined space. Some examples of devices having cavities that can be cleaned and sanitized by applying the present subject matter include like refrigerators, microwave ovens, food containers in any shape, containers of non-food items that needs cleaning and sanitization, storage and/or delivery boxes (not limited to food storage and/or delivery), and wash machines. Additionally, the present subject matter is not limited to spraying liquid hygiene agents but can also be used to spray various other liquid or gas such as pest control agents.

FIG. 1 is a block diagram illustrating an embodiment of a system 100 for cleaning and sanitizing a box 101. Box 101 can include any container having a cavity that needs to be cleaned and sanitized. In the illustrated embodiment, box 101 is a rectangular box with a flat, rectangular bottom 102 (only edges shown in FIG. 1), a lid (or cover) 103, and four sides. The four sides include a front side 105 (only an edge shown in FIG. 1), a rear side 104, and 2 lateral sides 106A and 106B (only an edge shown in FIG. 1) each coupled between front side 105 and rear side 104. Lid 103 is connected to rear side 104 with hinges 107A and 107B. In various embodiments, lid 103 is connected to rear side 104 with one or more hinges. Box 101 can be securely closed using a locking mechanism (not shown) that locks lid 103 in a closed position. When lid 103 is in the closed position (as shown in FIG. 1), a confined space is formed by interior surfaces of box 101, including interior surfaces of bottom 102, front side 105, rear side 104, lateral sides 106A and 106B, and lid 103. This confined space can be cleaned and sanitized by using the present subject matter.

An example of box 101 is a food storage and/or delivery box such as a portable food delivery box. In various embodiments, box 101 as a food delivery box can be carried by hand and/or attached onto a vehicle such as a bicycle, a moped, or a motorcycle. For example, the food delivery box can be attached onto the vehicle with rear side 104 facing the forward-moving direction of the vehicle. In various embodiments, box 101 is used to contain packaged foods without direct contact between the foods and the interior surfaces of the box. When being used properly, no solid or liquid food waste or stain should remain on the interior surfaces of box 101 so that no rinse is needed for cleaning. Manual cleaning may be needed in case of an accidental food spill.

System 100 can be an automatic hygiene system that includes a hygiene device 110, a user interface device 120, and an analysis center 124 that can communicate with user interface device 120 through a network 122. Hygiene device 110 can be attached to box 101. In some embodiments, hygiene device 110 is configured to be detachably attached to box 101. In the illustrated embodiment, hygiene device 110 includes a container unit 111 to contain a hygiene agent, a controller unit 112 to control delivery of the hygiene agent to a spray nozzle (not shown in FIG. 1), tubing 113 between container unit 111 and controller unit 112, and tubing 114 between controller unit 112 and the spray nozzle. It should be understood that arrangement of system components (e.g., how the components of hygiene device 110 are physically arranged, housed, and attached to box 101) as shown in FIG. 1 and other figures in this document are each illustrated by way of example and not by way of restriction. Such arrangement can be determined based on design considerations such as a specific shape and size of box 101 and where box 101 is to be placed and/or how box 101 is to be transported.

User interface device 120 is capable of transmitting and receiving information via one or more wireless communication links, such that it can present instructions to a user of box 101 and receive confirmation and/or commands from the user. In this document, a "user" includes a person who uses system 100 to clean and sanitize box 101. When box 101 is a portable food delivery box, the user may be a delivery person (also referred to as "driver", "rider", etc.) who is assigned the task of cleaning and/or sanitizing the box. Such a delivery person can include any person carrying the box by hand and/or using any vehicle. User interface device 120 can communicate with hygiene device 110 via a wireless communication link 121 (e.g., using Bluetooth technology), and can communicate with network 122 via another wireless communication link 123 (e.g., the Internet through Wi-Fi, or a cellular network). In various embodiments, user interface device 120 can present the instructions to the user using a touchscreen and/or a speaker and can receive the confirmation and/or commands from the user using the touchscreen and/or a microphone. For example, communicating with the user using the speaker and the microphone (e.g., a headphone set with a microphone) allows for hand-free operation at least to some extent. In various embodiments, user interface device 120 includes a mobile device such as a cellphone or a tablet computer.

Analysis center 124 can represent one or more data analysis and/or monitoring facilities that communicate with many boxes of a business organization, such as all the food delivery boxes of a food delivery company, or a subset such as all the food delivery boxes within a region or a subsidiary of the food delivery company. This allows the organization to efficiently and effectively manage the cleaning and/or sanitization of the boxes, such as for ensuring food safety and/or meeting regulatory requirements.

Network 122 can represent any network including, but not limited to, a telecommunication network, a local network, the Internet, or the Internet of Things (IoT). In various embodiments, network 122 includes the IoT with user interface device 120 and analysis center 124 each being part of it. In some embodiments, hygiene device 110 can communicate with network 122 directly (without user interface device 120) via another wireless communication link 127 (e.g., Wi-Fi or cellular network). This allows for communication between analysis center 124 or other operation control or management centers and hygiene device 110 directly when, for example, communication with user interface device 120 via links 121 and/or 123 is unavailable for any reason. In some embodiments, hygiene device 110 can be configured to be part of the IoT, and network 122 can represent the IoT, with hygiene device 110, user interface device 120, and analysis center 124 each being part of it.

Figure 2:
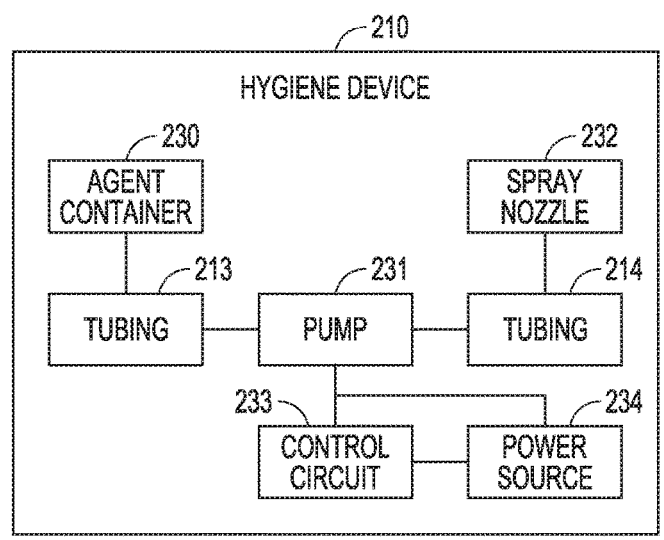
FIG. 2 is a block diagram illustrating an embodiment of a hygiene device of the system of FIG. 1.

FIG. 2 is a block diagram illustrating an embodiment of a hygiene device 210, which represents an example of components of hygiene device 110. Hygiene device 210 can include an agent container 230, tubing 213, a pump 231, tubing 214, a spray nozzle 232, a control circuit 233, and a power source 234.

Agent container 230 contains the hygiene agent. Depending on the purpose of conducting hygiene cycles, the hygiene agent can be a liquid chemical agent that has cleaning effects only, sanitization effects only, or both cleaning and sanitization effects. A hygiene agent that has both cleaning and sanitization effects can be referred to as a 2-in-1 hygiene agent or 2-in-1 C&S agent. Using such a 2-in-1 hygiene agent allow each C&S hygiene cycle to be performed with a single spraying action. In various embodiments, agent container 230 includes a refillable or disposable bottle suitable for containing the hygiene agent. Pump 231 can receive the hygiene agent from agent container 230 through tubing 213 and deliver the hygiene agent to spray nozzle 232 through tubing 214. An example of pump 231 includes a diaphragm pump. Spray nozzle 232 works with pump 213 to produce a mist of the hygiene agent in a confined space of a box such as box 101 to result in substantially uniform distribution of the hygiene agent on the interior surfaces of the box. In one embodiment as a specific example discussed in this document, spray nozzle 232 includes a single nozzle incorporated into the bottom of the box, such as by inserting into the box through a hole in a geometric center of the bottom of the box. In various embodiments, spray nozzle 232 can include one or more spray nozzles incorporated into the bottom, the lid, and/or each side of the four sides of the box to produce a mist of the hygiene agent in the box to result in substantially uniform distribution of the hygiene agent on the interior surfaces of the box. Control circuit 233 can include an electronic circuit configured to control conduction of the hygiene cycles. Power source 234 provides power for the operation of hygiene device 210. Power source 234 can include one or more rechargeable and/or non-rechargeable batteries.

In one embodiment, the components of hygiene device 210 are arranged and attached to the box as illustrated in FIG. 1, with container unit 111 including agent container 230, tubing 113 corresponding to tubing 213, controller unit 112 including pump 231, control circuit 233, and power source 234, tubing 114 corresponding to tubing 214, and spray nozzle 232 installed at bottom 102. In various embodiments, the components of hygiene device 210 can be arranged and coupled to the box in any way that ensures portability of the box.

Figure 3:
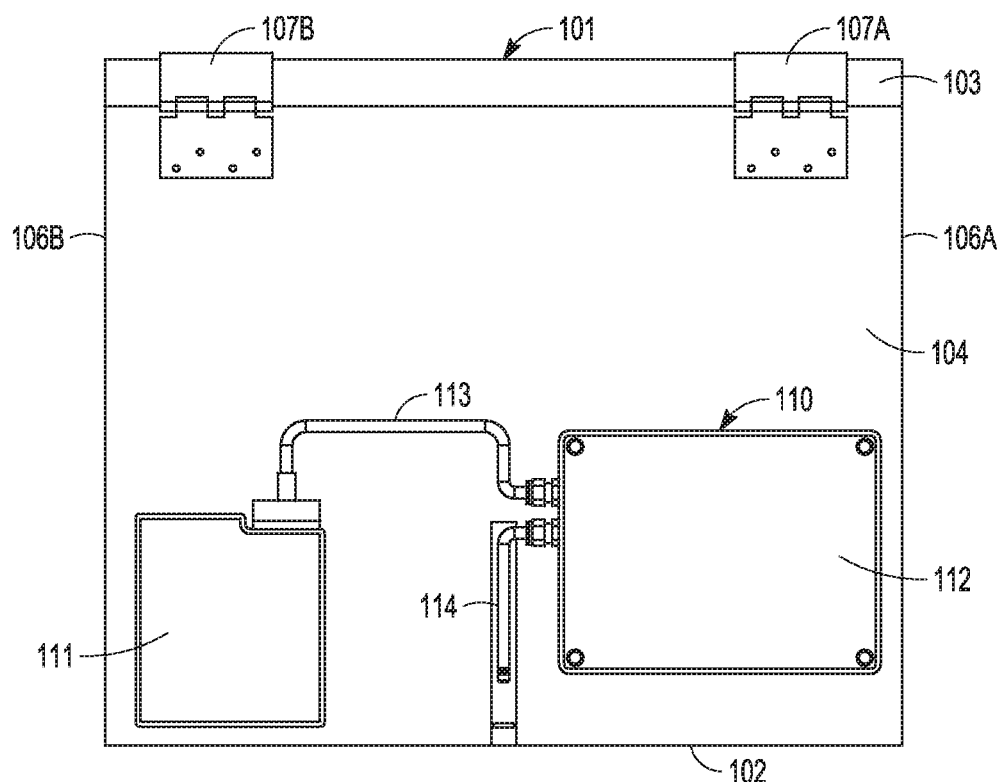
FIG. 3 is a diagram illustrating of an embodiment of portions of the hygiene device as seen from a rear view of the box.

FIG. 3 is a diagram illustrating of an embodiment of portions of hygiene device 110 as seen from a rear view of box 101. Components of box 101 that are shown in FIG. 3 include bottom 102 (only an edge shown), lid 103 (only an edge shown), lateral sides 106A (only an edge shown) and 106B (only an edge shown), and rear side 104. Components of hygiene device 110 that are shown in FIG. 3 include container unit 111, tubing 113, controller unit 112, and tubing 114.

Figure 4:
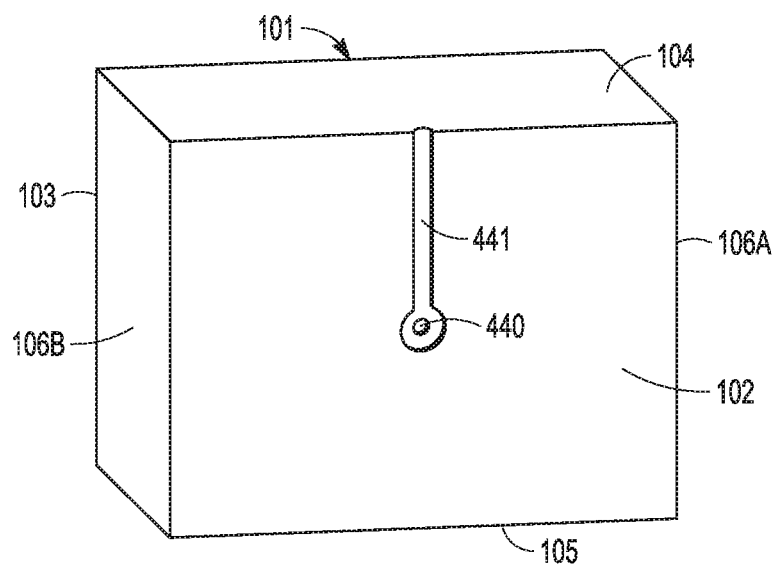
FIG. 4 is a diagram illustrating of an embodiment of a bottom of the box configured to accommodate a spray nozzle of the hygiene device.

FIG. 4 is a diagram illustrating of an embodiment of bottom 102 of box 101 configured to accommodate a spray nozzle. Components of box 101 that are shown in FIG. 4 include bottom 102, lid 103 (only two edges shown), rear side 104, front side 105 (only two edges shown), and lateral sides 106A (only two edges shown) and 106B. Bottom 102 includes a hole 440 sized and shaped to allow placement of the spray nozzle such as spray nozzle 232. Bottom 102 also includes a groove 441 to accommodate a portion of tubing 114 that is connected to the spray nozzle.

Figure 5:
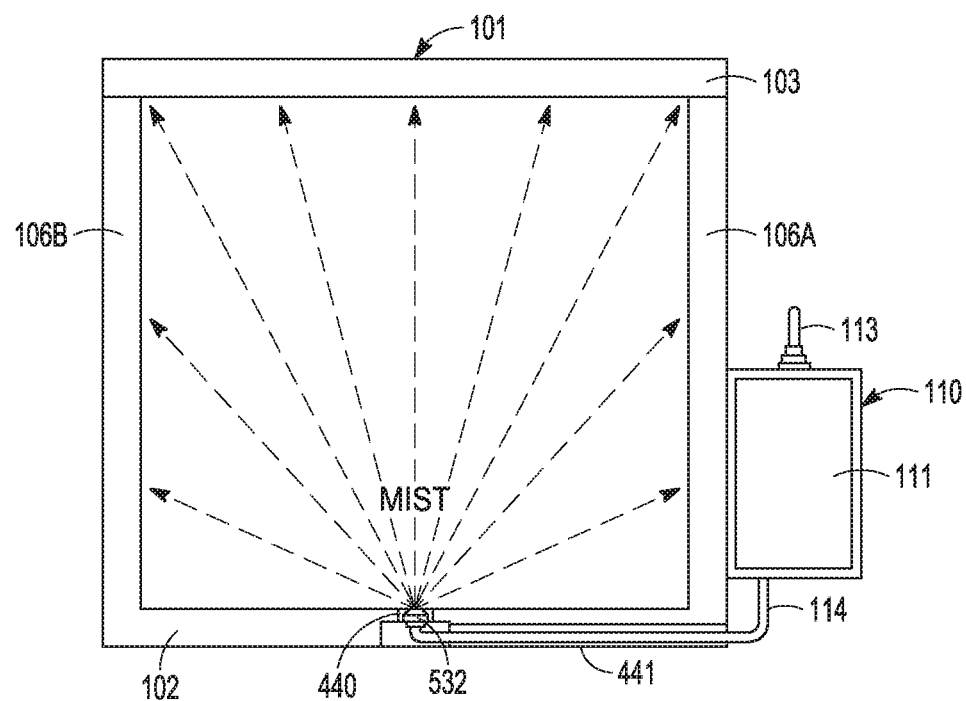
FIG. 5 is a diagram illustrating of an embodiment of portions of the hygiene device as seen on a cross-sectional view of the box.

FIG. 5 is a diagram illustrating of an embodiment of portions of hygiene device 110 as seen on a cross-sectional view of box 101. Components of box 101 that are shown in FIG. 5 include bottom 102 with hole 440 and groove 441, lid 103, and lateral sides 106A and 106B. Components of hygiene device 110 that are shown in FIG. 3 include container unit 111, tubing 113, tubing 114, and a spray nozzle 532 representing an example of spray nozzle 232 and shown as producing a mist distributing the hygiene agent onto the interior surfaces of box 101.

Figure 6:
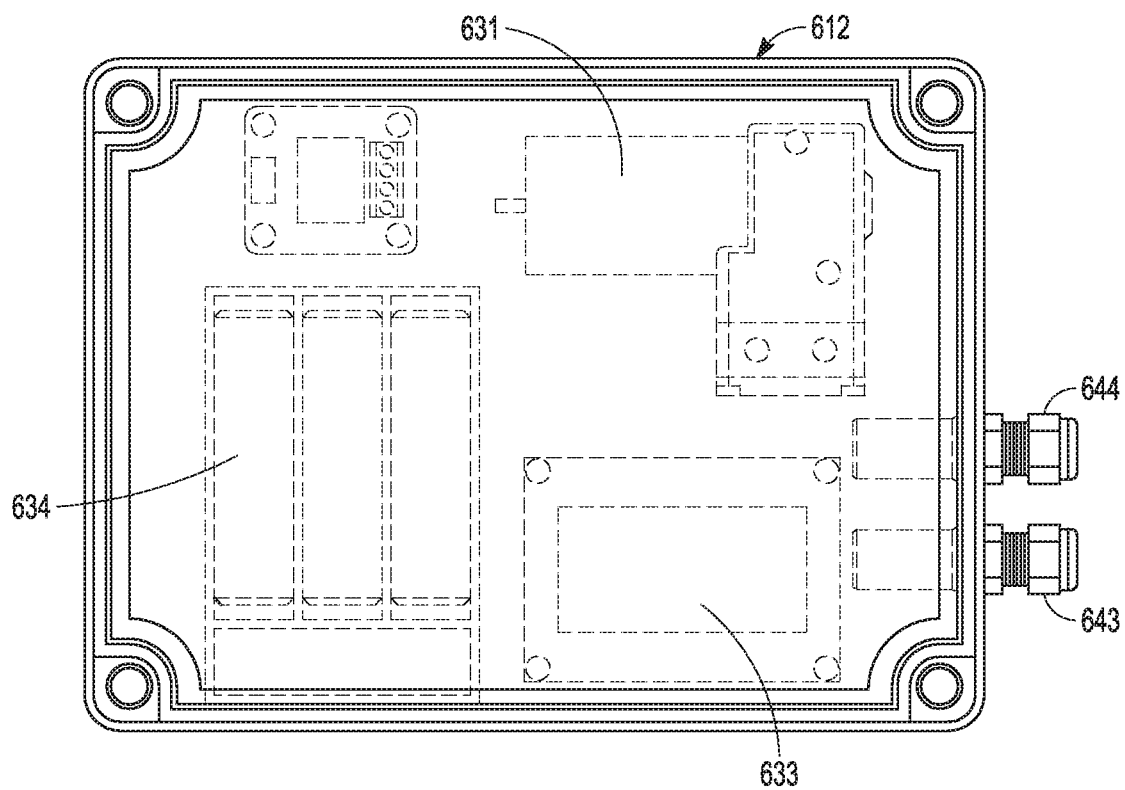
FIG. 6 is a diagram illustrating of an embodiment of a controller unit of the hygiene device.

FIG. 6 is a diagram illustrating of an embodiment of a controller unit 612, which represent an example of controller unit 112. Controller unit 612 as illustrated in FIG. 6 shows an example of placement of its major components including a pump 631 (representing an example of pump 231), a control circuit 633 (representing an example of control circuit 233), a battery pack 634 (representing an example of power source 234), a tubing connector 643 configured to connect to tubing 113, and a tubing connector 644 configured to connect to tubing 114.

Figure 7:
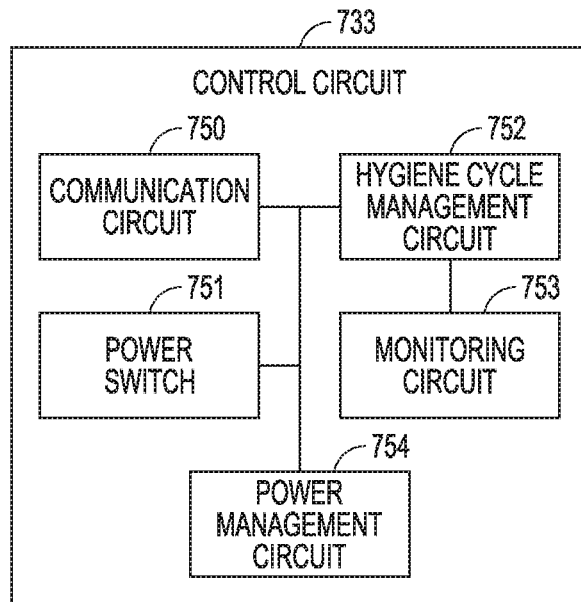
FIG. 7 is a block diagram illustrating an embodiment of a control circuit of the hygiene device.

FIG. 7 is a block diagram illustrating an embodiment of a control circuit 733, which represent an example of control circuit 233. Control circuit 733 can include a communication circuit 750, a power switch 751, a hygiene cycle management circuit 752, a monitoring circuit 753, and a power management circuit 754.

Communication circuit 750 provides for communication between user interface device 120 and hygiene device 110 via wireless communication link 121, such as using Bluetooth or Bluetooth Low Power (BLE) technology. In various embodiments, communication circuit 750 transmits data collected by hygiene device 110 to user interface device 120, receives commands controlling operation of hygiene device 110 from user interface device 120, and transmits signals indicative of operational status of hygiene device 110 to user interface device 120. User interface device 120 can function as a relay device for communications between hygiene device 110 and analysis center 124 (or any other operation control or management center) through network 122. In some embodiments, communication circuit 750 also provides for communication between network 122 and hygiene device 110 via wireless communication link 123, such as using Wi-Fi or a cellular network. Communication circuit 750 can transmit data collected by hygiene device 110 to analysis center 124, receive commands controlling operation of hygiene device 110 from analysis center 124, and transmit signals indicative of operational status of hygiene device 110 to analysis center 124, through network 122 without using user interface device 120 as a relay device.

Power switch 751 can include any switch suitable for turning electric power on and off. This allows the user to turn hygiene device 110 on and off.

Hygiene cycle management circuit 752 can initiate and control a hygiene cycle according to programmed schedule, criteria, and/or user command. In various embodiments, hygiene cycle management circuit 752 can be configured to initiate a hygiene cycle periodically (e.g., every 4 hours) or according to a specified (e.g. programmable) schedule (e.g., at 10:30 am, 2:00 pm, 5:00 pm, and 8:00 pm). Hygiene cycle management circuit 752 can also be configured to initiate a hygiene cycle in response to a user command (e.g., overriding the specified schedule). The user command can include a command transmitted from user interface device 120 and received by communication circuit 750. In various embodiments, hygiene cycle management circuit 752 can confirm that box 101 is empty and that lid 103 is closed and can start spraying the hygiene agent upon the confirmation. For example, hygiene cycle management circuit 752 can transmit a confirmation request signal through communication circuit 750 to user interface device 120 and receive a confirmation response signal confirming that box 101 is empty and that lid 103 is closed from user interface device 120. User interface device 120 can present the confirmation request signal as an audial and/or visual message to the user and receive the response from the user as the confirmation response signal. The confirmation response signal can act as a command for starting the spraying of the hygiene agent, i.e., hygiene cycle management circuit 752 can start spraying the hygiene agent upon receiving the confirmation response signal. In various embodiments, hygiene cycle management circuit 752 can also control the performance of the hygiene cycle following its initiation, including controlling the pumping of the hygiene agent during the hygiene cycle. For example, hygiene cycle management circuit 752 can control the duration of the pumping of the hygiene agent by timing the pumping and ending the pumping when a specified time interval expires.

Monitoring circuit 753 can record information indicative of performance of each hygiene cycle and transmit the recorded information to network 122 (in other words, "upload data to the cloud"). In various embodiments, the recorded information can include information identifying box 101 (e.g., a serial number), the user (e.g., the delivery person using the box), time of the hygiene cycle (e.g., starting, ending, and/or actual spraying times), and/or location where the hygiene cycle is conducted. In various embodiments, the recorded information is transmitted to network 122 such that analysis center 124 can analyze the recorded information and send instructions and/or warnings to user interface device 120 based on an outcome of the analysis (e.g., to ensure compliance of hygiene procedures), receive recorded information from all the delivery boxes equipped with the hygiene devices (e.g., company-wide, region-wide, or nationwide) on a regular basis, report performance (e.g., statistical data) of the hygiene cycles for the delivery boxes to management (e.g., a designated person or team) periodically (e.g., monthly), and/or send instructions to each user and/or each team leader managing a plurality of users from the management. In various embodiments, monitoring circuit 753 can also monitor the status of the hygiene cycle and notify the user by transmitting information indicative the status of the hygiene cycle to user interface device 120. When the transmitted information indicates that the hygiene cycle is completed, user interface device 120 can present an instruction for the user to open lid 103 to allow natural drying or to use paper towel to wipe the interior surfaces of box 101 upon completion of the hygiene cycle (e.g., for compliance with regulatory requirement) and/or to perform certain other tasks in compliance with pertinent regulatory requirements.

Power management circuit 754 can manage the operation of power source 234 and control distribution of electric power to various components of hygiene device 110 that require the electric power to function (e.g., pump 231 and control circuit 233 or 733). When power source 234 includes one or more batteries, power management circuit 754 can monitor the remaining level of the one or more batteries and produce a battery level alter signal in response to the level dropping under a battery level threshold. Power management circuit 754 can transmit this battery level alert signal though communication circuit 750 to user interface circuit 120 to remind the user to replace or recharge the one or more batteries of power source 234. In one embodiment, the user interface device 120 reminds the user to replace or recharge the battery periodically (e.g., weekly).

In some embodiments, control circuit 733 is configured to determine the location of hygiene device 110 using a positioning system such as the global positioning system (GPS) or location-based services (LBS). This allows for tracking of hygiene device 110 and use of its location tracks to determine whether a hygiene cycle should be conducted. Hygiene cycle management circuit 752 can use the location of hygiene device 110 as one of the criteria to initiate the hygiene cycle. For example, when box 101 is due for a scheduled hygiene cycle, hygiene cycle management circuit 752 can track the location of the attached hygiene device 110 and initiate the hygiene cycle after box 101 with hygiene device 110 returns after a food delivery to a facility while the delivered foods are prepared. The information about the hygiene cycle recorded and transmitted by monitoring circuit 753 can also include the location where the hygiene cycle is conducted. Control circuit 733 and/or analysis center 124 can analyze the recorded information to determine whether the hygiene procedure is complied, for example, by determining the number of food deliveries (as monitored by tracking locations of hygiene device 110) between two hygiene cycles. Control circuit 733 can also send information indicating location of hygiene device 110 to network 122 to allow for tracking of hygiene device 110 by analysis center 124 and/or other operation control or management centers for various other purposes. For example, the location of hygiene device 110 can be tracked for recording and analyzing routes of food delivery to improve timing or efficiency, or to monitor whether hygiene device 110 is deployed in compliance of the hygiene procedure.

In various embodiments, control circuit 733 can include one or more switches or a control panel that allow the user to manually control certain functions of controller unit 612, for example when communication between user interface device 120 and hygiene device 110 is unavailable or when a hygiene cycle fails to be initiated automatically for any reason. The user can manually start the hygiene cycle, for example, upon receiving a reminder for manually starting the hygiene cycle or a message that a scheduled hygiene cycle has not started on time.

Figure 8:
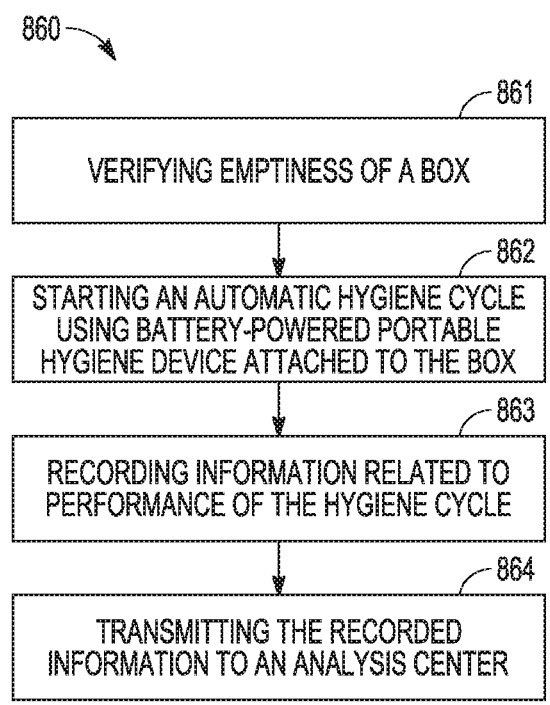
FIG. 8 is a flow chart illustrating an embodiment of a method for cleaning and sanitizing a box.

FIG. 8 is a flow chart illustrating an embodiment of a method 860 for cleaning and sanitizing a box, such as box 101. In one embodiment, system 100 is configured for performing method 860. In one embodiment, a user interface device such as user interface device 120 is configured to control the performance of method 860. For example, the user interface device can include a cellphone, and an application is installed on the cellphone for controlling the performance of method 860. The application can present reminder and instructions to the user before, after, and during each hygiene cycle.

At 861, emptiness of the box is verified. If the box is not empty (e.g., food is contained in the box), the contents must be removed before a hygiene cycle can be started. If the box is not empty because it is dirty (e.g., resulting from food spill), the box can be manually cleaned (e.g., using a paper towel to wipe out solid or liquid food spills). Emptiness of the box can then be verified.

At 862, an automatic hygiene cycle is started in response to a command indicating the verification that the box is empty. The hygiene cycle can be automatically conducted using a battery-powered portable hygiene device attached to the box, such as hygiene device 110.

At 863, information related to performance of the hygiene cycle is recorded by the battery-powered portable hygiene device. Such information indicates whether a hygiene procedure is complied, for example for ensuring food safety and/or meeting regulatory requirements.

At 864, the recorded information is transmitted to an analysis center, such as by uploading data representing the recorded information to a network. This concludes the hygiene cycle. In various embodiments, the transmission of the recorded information can be triggered by end of each hygiene cycle, on a periodic basis, by a data transmission command transmitted from the user interface device, and/or by a detection of failure in complying with the hygiene procedure. The recorded information can be transmitted to the analysis center from the battery-powered portable hygiene device directly and/or via the user interface device.

In various embodiments, upon completion of the hygiene cycle, interior surfaces of the box are to be dried by the user. This can be done by opening the lid of the box to allow natural air dry. Alternatively, this can be done by opening the lid of the box and wiping all the interior surfaces of the box (e.g., using a paper towel), such as when time or weather does not allow for air dry. When the box is used for food delivery, no liquid (i.e., the hygiene agent) should remain in the box when loading packaged food for the next food delivery.

In various embodiments, exterior of the box is also to be cleaned periodically. Such cleaning can be performed manually.

In various embodiments in which the container of the hygiene agent is refillable, the container is to be cleaned before each refill or after a specified number of refills. Other parts of the hygiene device (e.g., the nozzle and/or the tubing) are also to be cleaned periodically or as needed.

Figure 9:
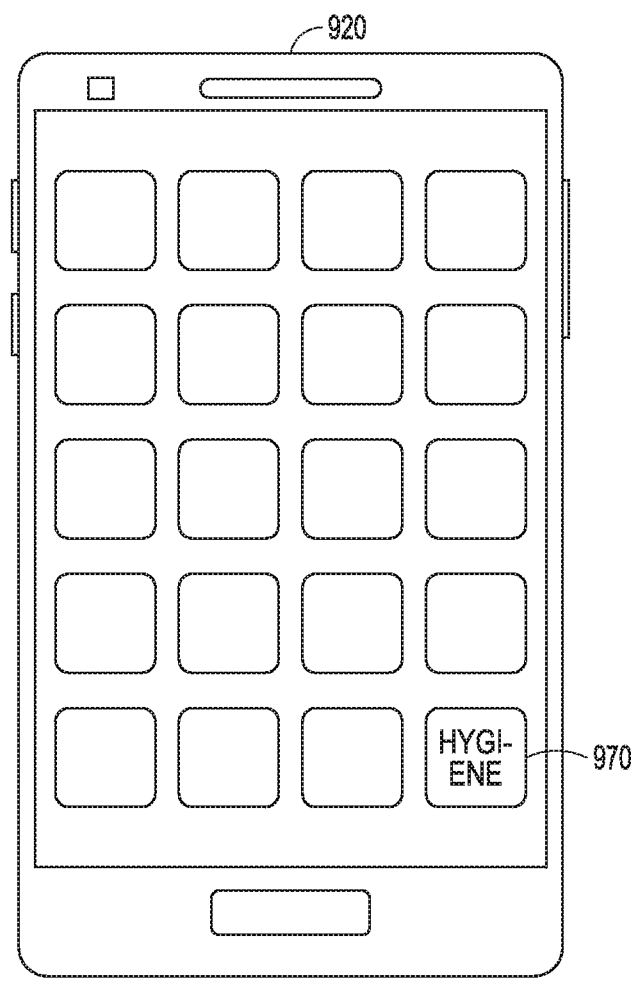
FIG. 9 is a diagram illustrating an embodiment of a user interface device of the system of FIG. 1.

FIG. 9 is a diagram illustrating an embodiment of a user interface device 920, which can represent an embodiment of user interface device 120. In the illustrated embodiment, user interface device 920 is a cellphone on which a hygiene application 970 is installed. The cellphone is to be carried by each delivery person (or another person) responsible for compliance with the hygiene procedure.

In various embodiments, functions performed by application 970 through cellphone 920 can include those selected from the following examples:

presenting food safety tips for home delivery of cooked food;

displaying a training video on a hygiene procedure for home delivery of cooked food;

reminding the user that a hygiene cycle is starting or to be started (with an audial and/or visual message);

instructing the user to check whether the box is empty;

receiving confirmation from the user that the box is empty;

triggering spray of the hygiene agent during each hygiene cycle;

recording information related to each hygiene cycle;

sending the recorded information to the network (uploading data representative of the recorded information to the analysis center through the network as triggered by end of each hygiene cycle, on a periodic basis, by a transmission command from the user, and/or by a detection of failure in complying with a hygiene procedure;

detecting each failure in complying with the hygiene procedure;

receiving feedback information from the analysis center (the feedback information produced automatically by the data analysis center and/or by one or more persons such as the management); and presenting the feedback information (e.g., confirmation of compliance, reminder and/or instructions for actions by the user, and/or warnings related to each failure in complying with the hygiene procedure as detected by the application or the analysis center).

The above is not an exhaustive list, and other related functions may be included as determined by those skilled in the art.

Figure 10:
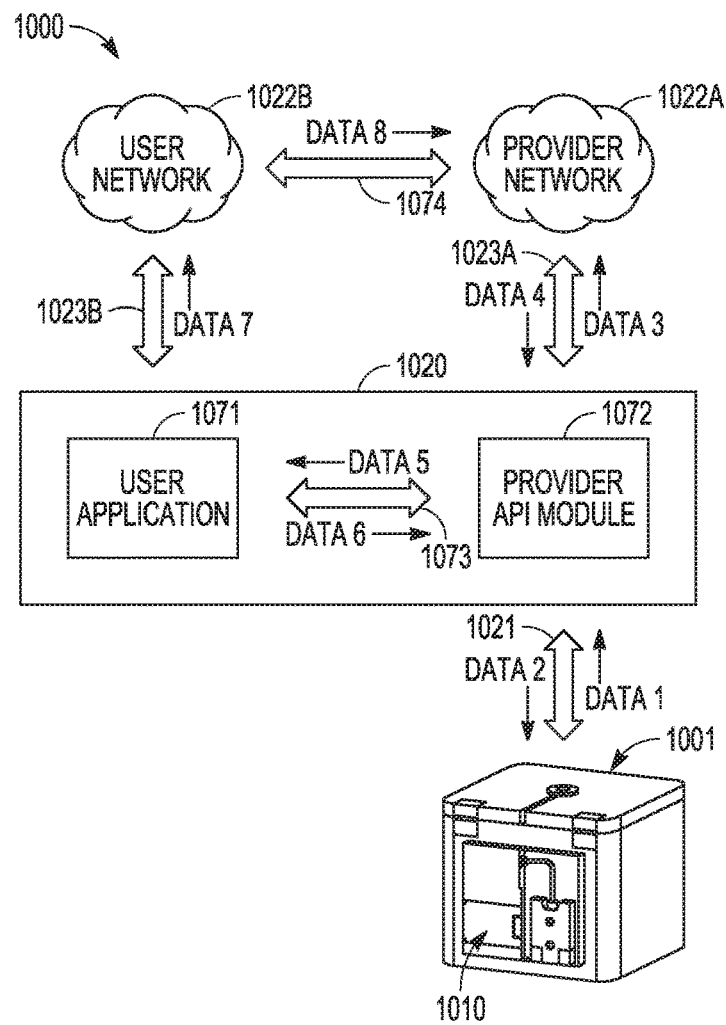
FIG. 10 is a block diagram illustrating another embodiment of a system for cleaning and sanitizing a box using a hygiene device.

FIG. 10 is a block diagram illustrating an embodiment of a system 1000 for cleaning and sanitizing a box 1001 using a hygiene device 1010. System 1000 can represent an example of system 100 in which the present subject matter is implemented by a provider for use by a user. In the illustrated embodiment, system 1000 can be an automatic hygiene system that includes a hygiene device 1010, a user interface device 1020, a provider network 1022A, and a user network 1022B. In this document, a "provider" develops system such as systems 100 and 1000, or portions thereof, according to various embodiments of the present subject matter. The user can be part of an organization of users each using the system provided by the provider. For example, the provider can include a company that provides hygiene systems for food hygiene, and each user can be a food delivery person of a food delivery company using the system provided by the provider for cleaning and/or sanitizing a portable food delivery box. The food delivery company can be a customer of the provider company. Provider network 1022A (which can be referred to as "provider's cloud") can include a network owned by operated by the provider. User network 1022B can include a network owned by operated by the user or the organization of the users.

Box 1001 can include any container having a cavity that needs to be cleaned and sanitized and can represent an example of how box 101 may be implemented according to the present subject matter. Hygiene device 1010 can represent an example of how hygiene device 110 may be implemented according to the present subject matter. Details of box 1001 and hygiene device 1010 are further discussed below with reference to FIGS. 12-20. It should be understood that while box 1001 and hygiene device 1010 are illustrated as part of system 1000, they are not limited to be part of system 1000 but can be used in system 100 or any system within the present subject matter.

User interface device 1020 can represent an example of user interface device 120 implemented for use by the user in the embodiment illustrated in FIG. 10, with the provider and the user. User interface device 1020 can be a dedicated device configured to be carried by the user or a mobile phone installed with applications implemented according to the present subject matter. User interface device 1020 can communicate with hygiene device 1010 via a wireless communication link 1021, communicate with provider network 1022A via another wireless communication link 1023A, and communicate with user network 1022B via another wireless communication link 1023B. Wireless communication link 1021 can be implemented using, for example, Bluetooth or BLE technology. Wireless communication links 1023A-B can each be implemented using, for example, a cable, a Low Power Wide Area Network (LP-WAN), a wireless Local Area network (LAN), and/or a cellular network. Examples of LPWAN include Long Range (LoRa) and Narrowband Internet of Things (NB-IoT). Examples of the wireless LAN include WiFi and BLE technologies. The cellular network in this document can include a communication network using any generation of cellular technology (e.g., 2G-5G). For example, data can be transmitted to provider network 1022A using the cellular network, and transmitted out of provider network 1022A using the cable, LPWAN, and/or LAN.

In the illustrated embodiment, user interface device 1020 includes a provider application programming interface (API) module 1072 and a user application 1071 connected to each other via a data link 1073. In various embodiments, the provider provides a software development kit (SDK) using which API module 1072 can be developed. In some embodiments, the user or the organization of the users can be provided with the SDK for developing user application 1071, which can call API module 1072 via data link 1073 to communicate with hygiene device 1010. The SDK can contain all the files and functions that API module 1072 connects to and can be used by different users to develop different versions of user application 1071.

Provider network 1022A and user network 1022B can represent examples of portions of network 122 and analysis center 124. For example, user network 1022B may be primarily used for managing a food delivery business, while the provider network 1022A cooperates with user network 1022B through a communication link 1074 to manage the cleaning and/or sanitization of the packaged food containing boxes of the food delivery business. In various embodiments, provider network 1022A can include functions of analysis center 124 for ensuring food safety and/or meeting regulatory requirements for the food delivery business. In various embodiments, analysis center 124 can perform data analysis and machine learning to get actionable insights from various information received from user interface device 1020 and/or box 1001 and to optimize the performance of system 1000 including various operational parameters controlling performance of the hygiene cycles (e.g., the duration of spray and frequency of the hygiene cycles).

Examples of data transmitted within system 1000 can include, but are not limited to, data representing the following information:

DATA 1 (data transmission from hygiene device 1010 to provider API module 1072 via communication link 1021): status of a hygiene cycle, battery level of hygiene device 1010, and indication that lid on box 1001 is open;

DATA 2 (data transmission from provider API module 1072 to hygiene device 1010 via communication link 1021): command to start a hygiene cycle, command for controlling pump timing in hygiene device 1010, universal time coordinated (UTC), and software upgrade for hygiene device 1010;

DATA 3 (data transmission from provider API module 1072 to provider network 1022A via communication link 1023A): the hygiene device battery level, the indication that lid on box 1001 is open, and data related to performance of a hygiene cycle;

DATA 4 (data transmission from provider network 1022A to provider API module 1072 via communication link 1023A): reminder for starting a hygiene cycle, the command for controlling pump timing in hygiene device 1010, the UTC, and software upgrade for provider API module 1072 and/or the SDK;

DATA 5 (data transmission from provider API module 1072 to user application 1071 via data link 1073): the reminder for starting a hygiene cycle, the status of a hygiene cycle, the battery level of hygiene device 1010, and the indication that lid on box 1001 is open;

DATA 6 (data transmission from user application 1071 to provider API module 1072 via data link 1073): the command to start a hygiene cycle;

DATA 7 (data transmission from user application 1071 to user network 1022B via communication link 1023B): the data related to performance of a hygiene cycle; and DATA 8 (data transmission from user network 1022 B to provider network 1022A via communication link 1074): the data related to performance of a hygiene cycle and the user's organizational information.

Figure 11:
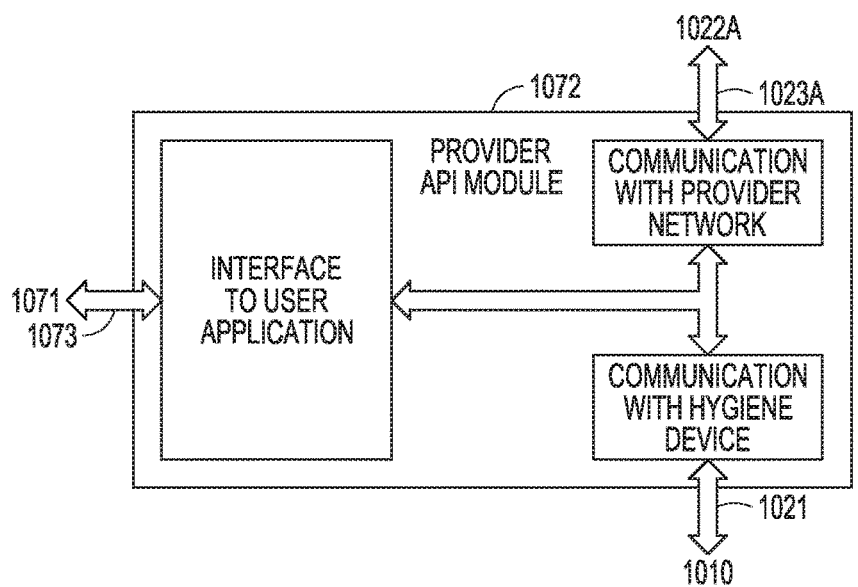
FIG. 11 is a block diagram illustrating an embodiment of an application programming interface (API) module of the system of FIG. 10.

FIG. 11 is a block diagram illustrating an embodiment of provider API module 1072. In the illustrated embodiment, provider API module 1072 provides for (1) interface to user application 1071 via data link 1073, (2) communication with hygiene device 1010 via communication link 1021, and (3) communication with provider network 1022A via communication link 1023A.

Figure 12:
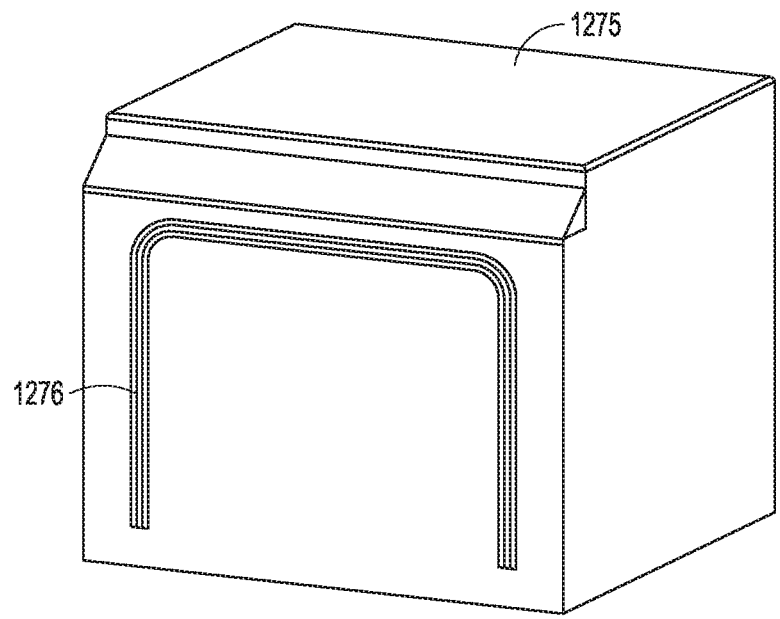
FIG. 12 is a diagram illustrating of an embodiment of a box cover as seen from its rear view.
Figure 13:
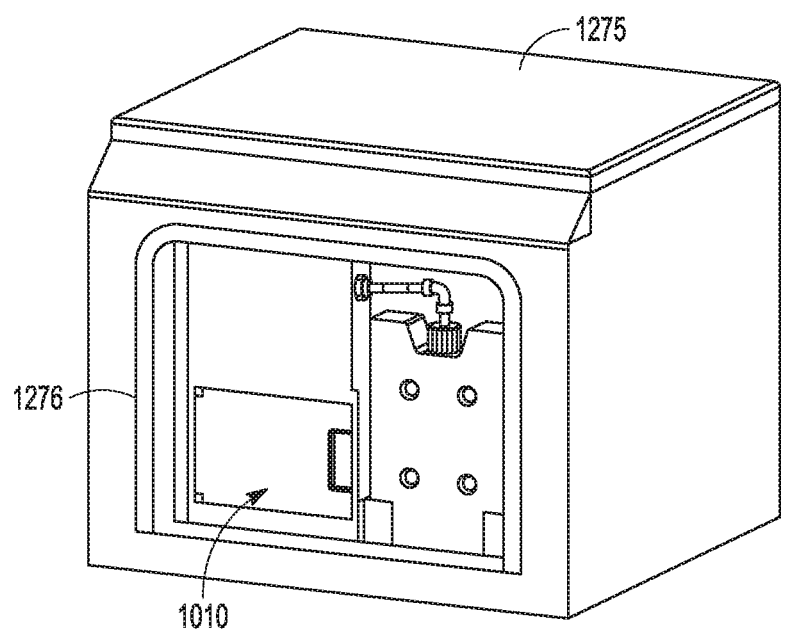
FIG. 13 is a diagram illustrating of an embodiment of the box cover of FIG. 12 showing the hygiene device of FIG. 10.

FIG. 12 is a diagram illustrating of an embodiment of a box cover 1275 as seen from its rear view. Box cover 1275 can provide protection of box 1001 and hygiene device 1010 from mechanical impact that may be encountered when box 1001 is being transported, such as during food delivery. Box cover 1275 can wrap the entire box 1001 and hygiene device 1010 (which is affixed onto box 1001), while allowing the lid of box 1001 to open, and can include a zipper 1276 to allow for access to hygiene device 1010 without unwrapping the entire box cover. FIG. 13 is a diagram illustrating of an embodiment of box cover 1275 with zipper 1276 being unzipped to show hygiene device 1010. This allows for easy access to hygiene device 1010 for replacing the battery and the bottle containing the hygiene agent, as discussed below.

Figure 14:
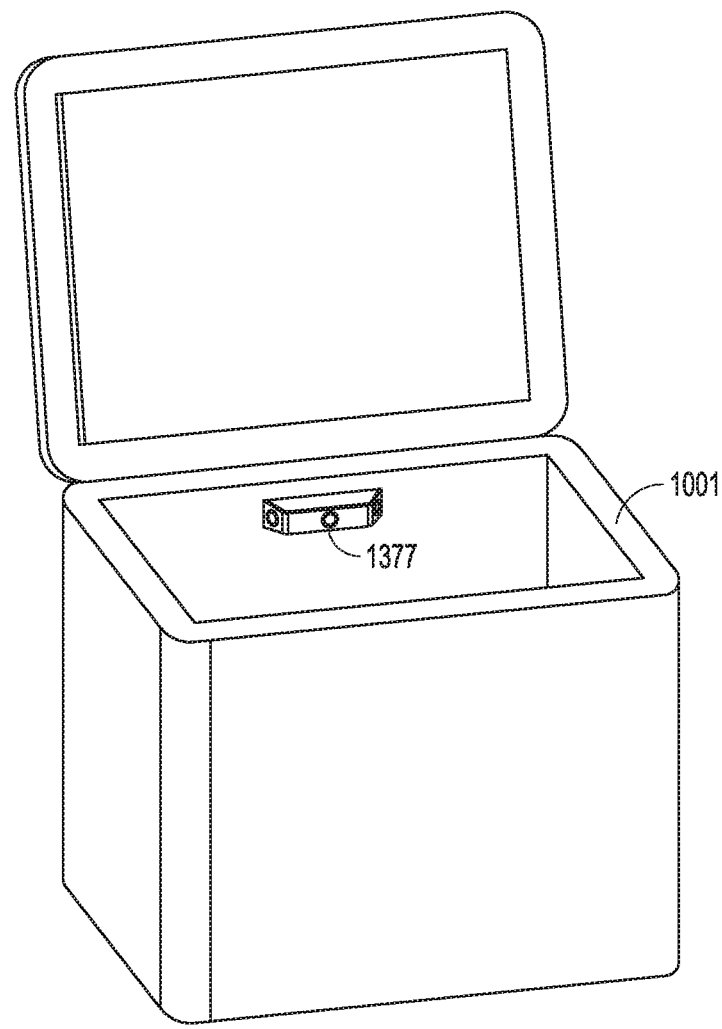
FIG. 14 is a diagram illustrating of an embodiment of the box of FIG. 10 showing a nozzle assembly of the hygiene device of FIG. 10.
Figure 15:
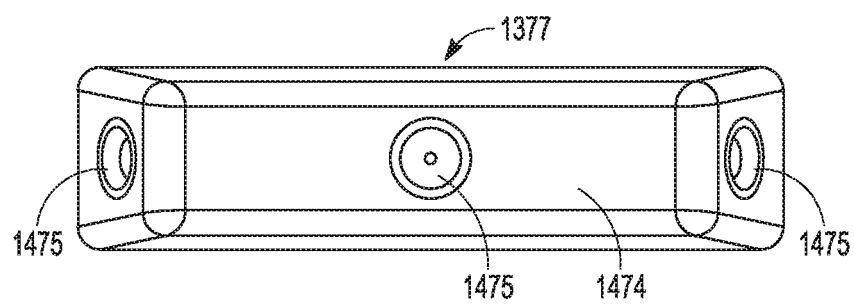
FIG. 15 is a diagram illustrating of an embodiment of the nozzle assembly of FIG. 14.

FIG. 14 is a diagram illustrating of an embodiment of box 1001 showing a nozzle assembly 1733 hygiene device 1010. In the illustrated embodiment, nozzle assembly 1733 in installed on the rear interior surface of box 1001 near the top (lid). FIG. 15 is a diagram illustrating of an embodiment of nozzle assembly 1377. In the illustrated embodiment, nozzle assembly 1377 includes three nozzles 1475 and a nozzle top cover 1474. Nozzles 1475 are distributed and oriented to spray the hygiene agent to cover all six interior surfaces of box 1001 while preventing the hygiene agent from contaminating the food contained in box 1001. Nozzle assembly 1377 is positioned, and nozzle top cover 1474 is shaped, to protect nozzles 1475 from being damaged during loading, unloading, and transportation of the containers of food to be delivered using box 1001, and to avoid scratching of these containers by nozzles 1475. Nozzle assembly 1733 represents a specific example of spray nozzle(s) according to the present subject matter, in addition to spray nozzle 232. In various embodiments, one or more spray nozzles are arranged inside box 1001 to result in a substantially uniform application of the hygiene agent on all the interior surfaces of box 1001 while minimizing interference with items to be contained in box 1001.

Figure 16:
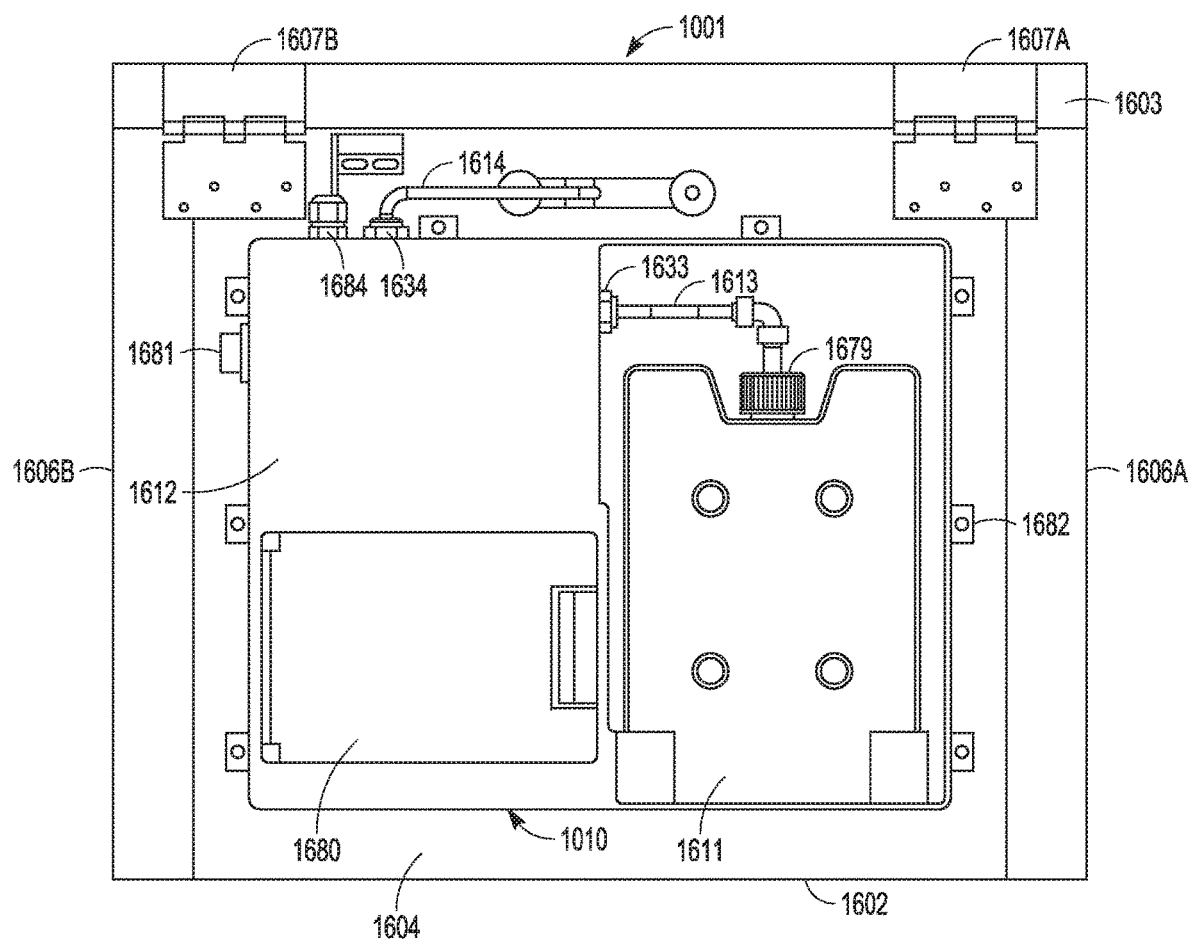
FIG. 16 is a diagram illustrating of an embodiment of portions of the hygiene device of FIG. 10 as seen from a rear view of the box of FIG. 10.

FIG. 16 is a diagram illustrating of an embodiment of portions of hygiene device 1010 as seen from a rear view of box 1001. In the illustrated embodiment, box 1001 is a rectangular box with a flat, rectangular bottom 1602 (only edges shown in FIG. 16), a lid (or cover) 1603, and four sides. The four sides include a front side (not shown in FIG. 16), a rear side 1604 (opposite of the front side), and 2 lateral sides 1606A and 1606B (only an edge shown in FIG. 16) each coupled between the front side and rear side 1604. Lid 1603 is connected to rear side 1604 with hinges 1607A and 1607B. In various embodiments, lid 1603 is connected to rear side 104 with one or more hinges. Box 1601 can be securely closed using a locking mechanism (not shown) that locks lid 1603 in a closed position. When lid 1603 is in the closed position (as shown in FIG. 16), a confined space is formed by interior surfaces of box 1601, including interior surfaces of bottom 102, the front side, rear side 1604, lateral sides 1606A and 1606B, and lid 1603. In the embodiment illustrated in FIG. 14, this confined space can be cleaned and sanitized by using the hygiene agent sprayed through nozzle assembly 1377 mounted on the interior surface of rear side 1604, in an upper-central location near the upper edge of rear side 1604.

Figure 17:
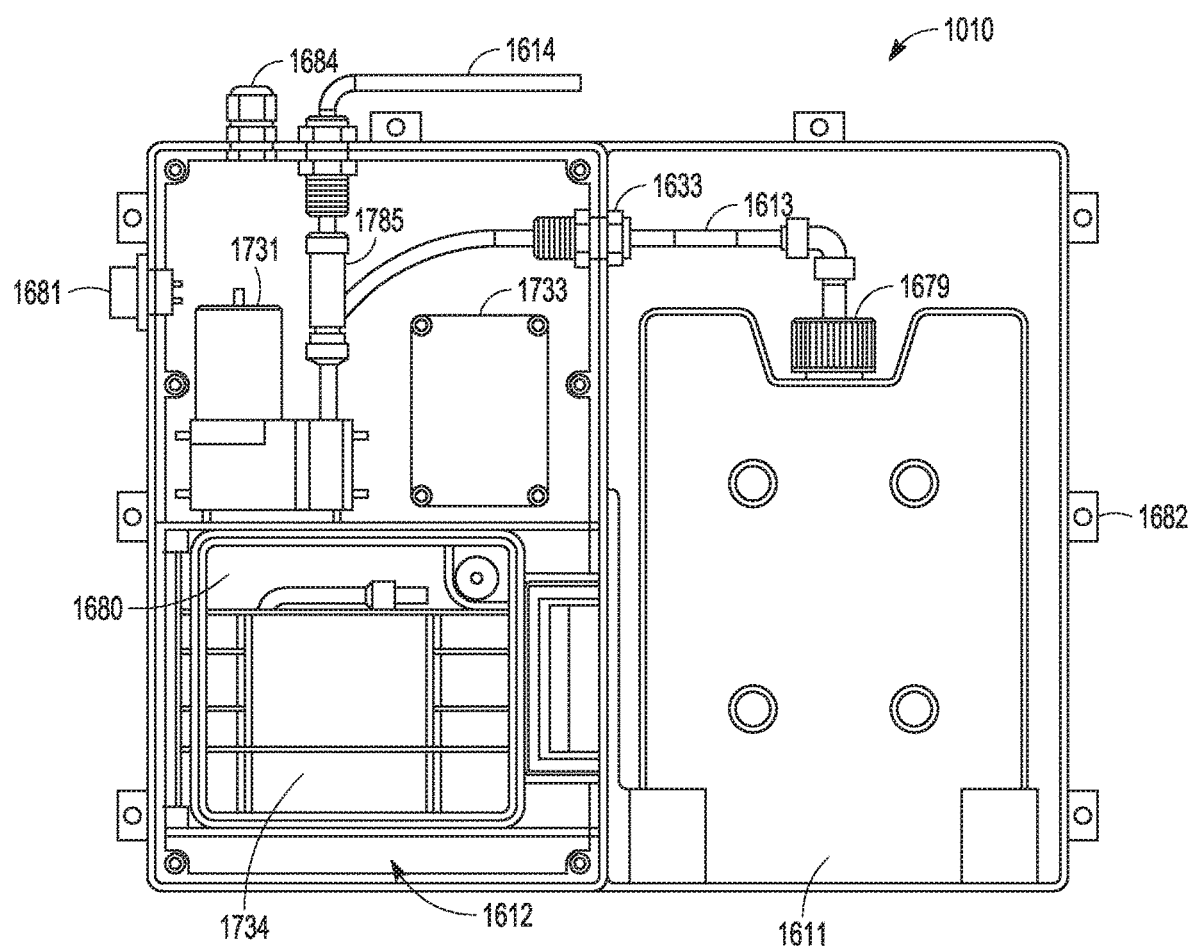
FIG. 17 is a diagram illustrating of an embodiment of portions of the hygiene device of FIG. 10 showing its internal components.

Hygiene device 1010 is mounted on the exterior surface of rear aide 1604 of box 1001. Hygiene device 1010 can include mounting tabs 1682, a control unit 1612, a container unit 1612, tubing 1613 between container unit 1611 and controller unit 1612, and tubing 1614 between controller unit 1612 and nozzles 1475 (shown in FIG. 14). FIG. 17 is a diagram illustrating of an embodiment of portions of hygiene device 1010 showing internal components of controller unit 1612 (which are not shown in FIG. 16). Such internal components include a pump 1731, a check valve 1785, a control circuit 1733, and a battery 1734.

Mounting tabs 1682 allow for tightly affixing major portions of hygiene device 1010 to rear side of box 1001. In the illustrated embodiment, 8 mounting tabs 1682 are distributed approximately evenly along 3 edges of hygiene device 1010. In various embodiments, hygiene device 1010 can include any number of mounting tabs 1682 distributed in a manner ensuring secure affixation of hygiene device 1010 onto box 1001. Control unit 1612 can represent an example of control unit 112 as implemented for system 1000 and can include a back cover 1680, a liquid inlet 1633, a liquid output 1634, a lid-open interlock 1684, and an externa port 1681. Back cover 1680 can be opened to remove battery 1734 from control unit 1612 for recharge or replacement. Liquid inlet 1633 can include a quick connector for connection with tubing 1613 to receive the hygiene agent from container unit 1611. Liquid outlet 1634 can include a quick connector for connection with tubing 1614 to transmit the hygiene agent to nozzles 1475. Lid-open interlock 1684 can detect open-close status of lid 1603 and stop the spraying of the hygiene agent from being transmitted to nozzles 1475 when lid 1603 is detected as being in a substantially open position. External port 1681 can receive external power. When external power is provided, for example through a power cord or cable connected to external port 1681, the power source for hygiene device 1010 can automatically switch from battery 1734 to the external power. In some embodiments, battery 1734 is a rechargeable battery, and control unit 1612 includes a battery charger to charge battery 1734 when the external power is provided. This allows for recharging of battery 1734 without removing it from hygiene device 1010. In some embodiments, control unit 1612 includes a wireless battery charging circuit to charge battery 1734 when being magnetically coupled to an external wireless charger. In various embodiments, battery 1734 is of a type that meets applicable government safety requirements. In various embodiments, battery 1734 is a rechargeable battery that can last at least 7 days between recharges when used for powering hygiene device 1010 for its normal use. Container unit 1611 can contain the hygiene agent. Container unit 1611 can be removed from hygiene device 1010 for refilling or replacement using a connector (cap) 1679. In the illustrated embodiment, container unit 1611, such as a bottle with cap 1679, can be removed from hygiene device 1010 for refill or replacement by loosening cap 1679 to disconnect the bottle from tubing 1613. In some other embodiments, connector 1679 can be configured to allow refill of container unit 1611 without removing it from hygiene device 1010.

Pump 1731 can represent an example of pump 633 as implemented for system 1000 and can include a diaphragm pump that is compatible with the hygiene agent. Pump 1731 can receive the hygiene agent from liquid inlet 1633 and pumps the hygiene agent out of controller unit 1612 through liquid outlet 1634. Check valve 1785 can prevent siphon and leakage of the hygiene agent. Control circuit 1733 can represent an example of control circuit 633 as implemented for system 1000 and can perform selected or all functions of control circuit 733 as discussed above. In various embodiments, control circuit 1733 can be constructed as a printed circuit board (PCB) and can support all the control functions of hygiene device 1010, including supporting the communication with provider API module 1072. In various embodiments, in addition to the functions of control circuit 633, control circuit 1733 can also be configured to perform functions including, but not limited to, batter power management, detection of level of the hygiene agent in container unit 1611 and producing warning signals indicating a need for refilling container unit 1611, and processing sensor signals from sensors installed in box 1001, such as temperature and/or humidity sensors. In various embodiments, one or more sensors are installed in or about box 1001 for monitoring various conditions of box 1001 and/or various operational statuses of box 1001. Example of such sensors include temperature senor, humidity sensor, odor sensor, light sensor, accelerometer, gyroscope, chemical inventory sensor, liquid pressure sensor, battery detection, and position sensor (e.g., GPS). In some embodiments, the one or more sensors installed in or about box 1001 can include a camera for remotely monitoring box 1001 and/or its surroundings and/or recording events occurring in and/or around box 1001. Battery 1734 can represent an example of battery 633 as implemented for system 1000 and can be a single battery or a battery pack that is rechargeable or non-rechargeable.

In various embodiments, circuits of systems 100 and 1000, including the various embodiments of their components discussed in this document, may be implemented using a combination of hardware and software. For example, the control circuits such as control circuits 233, 633, 733, and 1733 may each be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. In various embodiments, the control circuits each include storage media with flash memory and random-access memory (RAM) devices for storing instructions and parameters for performing control circuit functions.

Figure 18:
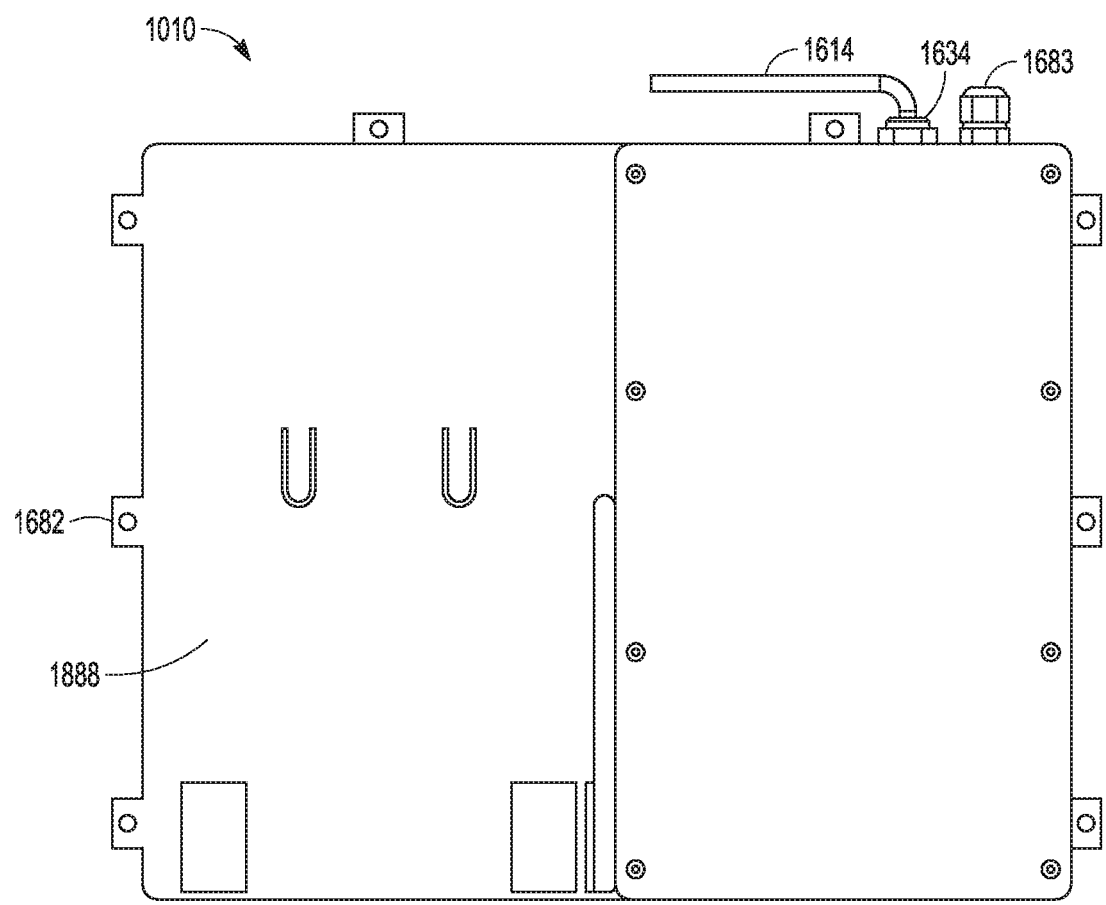
FIG. 18 is a diagram illustrating of an embodiment of portions of the hygiene device of FIG. 10 as seem from a direction opposite to that of FIG. 16.

FIG. 18 is a diagram illustrating of an embodiment of portions of hygiene device 1010 as seem from a direction opposite to that of FIG. 16. As illustrated in FIG. 18, hygiene device 1010 includes a back panel 1888 that is in tight contact with rear side 1604 of box 1001 when hygiene device 1010 is affixed onto box 1001.

Figure 19:
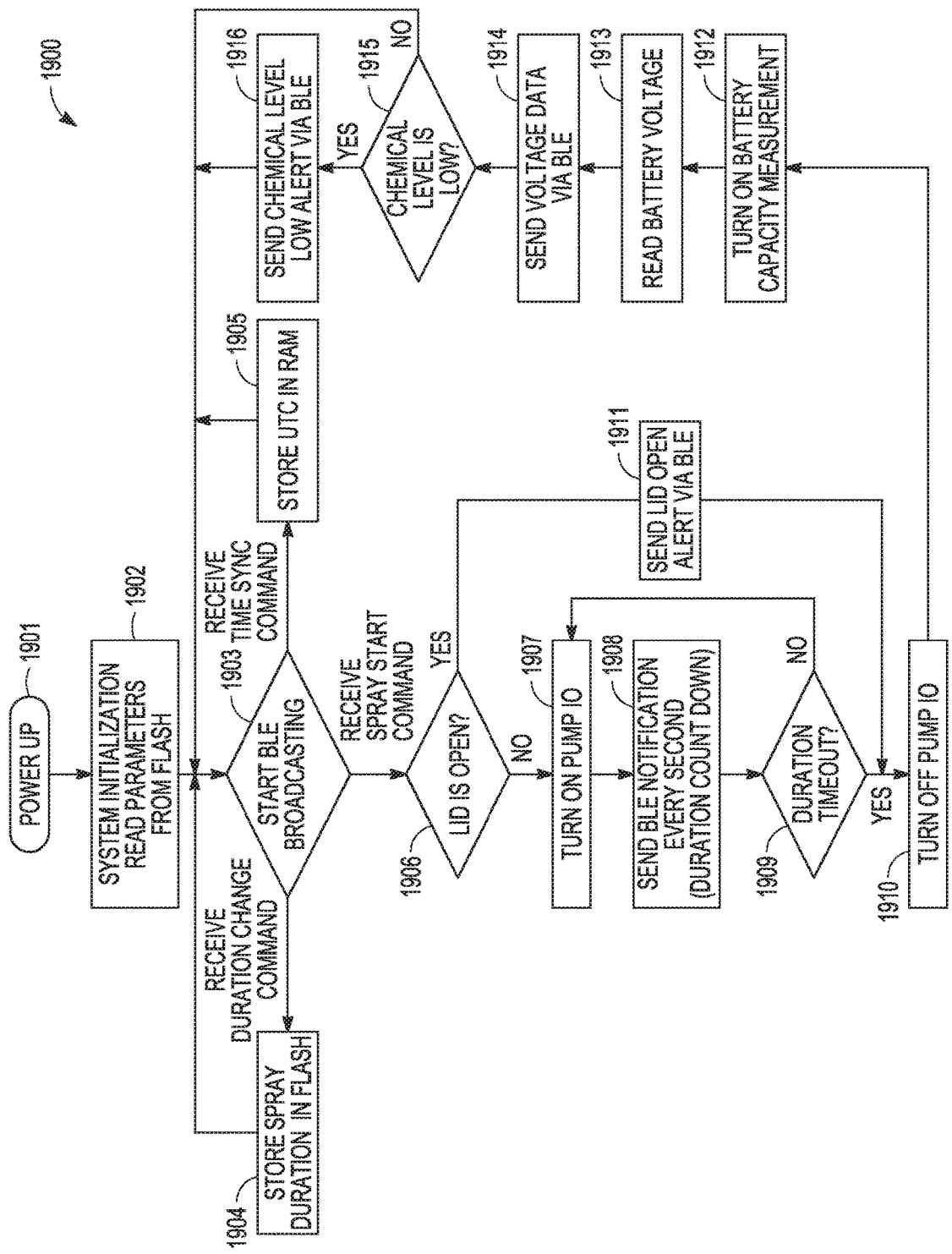
FIG. 19 is a flow chart illustrating an embodiment of a method for controlling conduction of hygiene cycles.

FIG. 19 is a flow chart illustrating an embodiment of a method 1900 for controlling hygiene cycles conducted by a hygiene device attached to a box to be cleaned and/or sanitized, such as hygiene device 1010 attached to box 1001. In one embodiment, a control circuit of the hygiene device, such as control circuit 1733, is programmed to perform method 1900. For example, method 1900 can be performed by the control circuit by executing instructions stored in a storage medium of the control circuit as firmware.

At 1901, the control circuit is turned on (powered up). At 1902, a system initialization is performed, during which parameters controlling a hygiene cycle is read from a flash memory of the control circuit. At 1903, BLE broadcasting is started (e.g., via communication link 1021). While a BLE connection is used as an example, any suitable wireless communication technology can be used to establish the wireless connection (e.g., communication link 1021) needed for performing method 1900.

At 1904, if a duration change command specifying a spray duration for the hygiene cycle is received via the BLE connection, the received spray duration is stored in the flash memory for use in the current and subsequent hygiene cycles. At 1905, if a time sync command with UTC (a time specified in UTC) is received via the BLE connection, the received UTC is stored in a RAM of the control circuit.

At 1906, if a spray start command is received via the BLE connection, whether the lid of the box is open is checked. At 1907, if the lid is not open, a pump input/output (IO) is turned on. At 1908, a notification that the pump IO is on is sent out (e.g., to provider API module 1072) via the BLE connection periodically (e.g., every second) as a spray duration countdown. At 1909, whether the spray duration has expired is checked. If the spray duration has not expired, the pump IO stays on. At 1910, if the spray duration has expired, the pump IO is turned off. At 1911, if the lid is open at 1906, a lid-open alert is sent out (e.g., to provider API module 1072) via the BLE connection, and the pump IO stays off.

At 1912, a battery capacity measurement is started for measuring the status of a battery of the hygiene device (e.g., battery 1734). At 1913, voltage of the battery is read. At 1914, the voltage of the battery as an indication of the status of the battery (e.g., which indicates whether the battery needs to be recharged or replaced) is sent out (e.g., to provider API module 1072) via the BLE connection. At 1905, whether a chemical level (i.e., the level of the hygiene agent in a container unit such as container unit 1611) is checked. At 1916, if the chemical level is low (e.g., falling below a specified threshold level), a chemical-level-low alert is sent out (e.g., to provider API module 1072) via the BLE connection.

In various embodiments, once the system initialization is performed at 1902, steps 1903-1916 repeat according to the parameters read from the flash memory until the control circuit is turned off (powered down). In various embodiments, the control circuit is turned on and off when the hygiene device is turned on and off.

Figure 20:
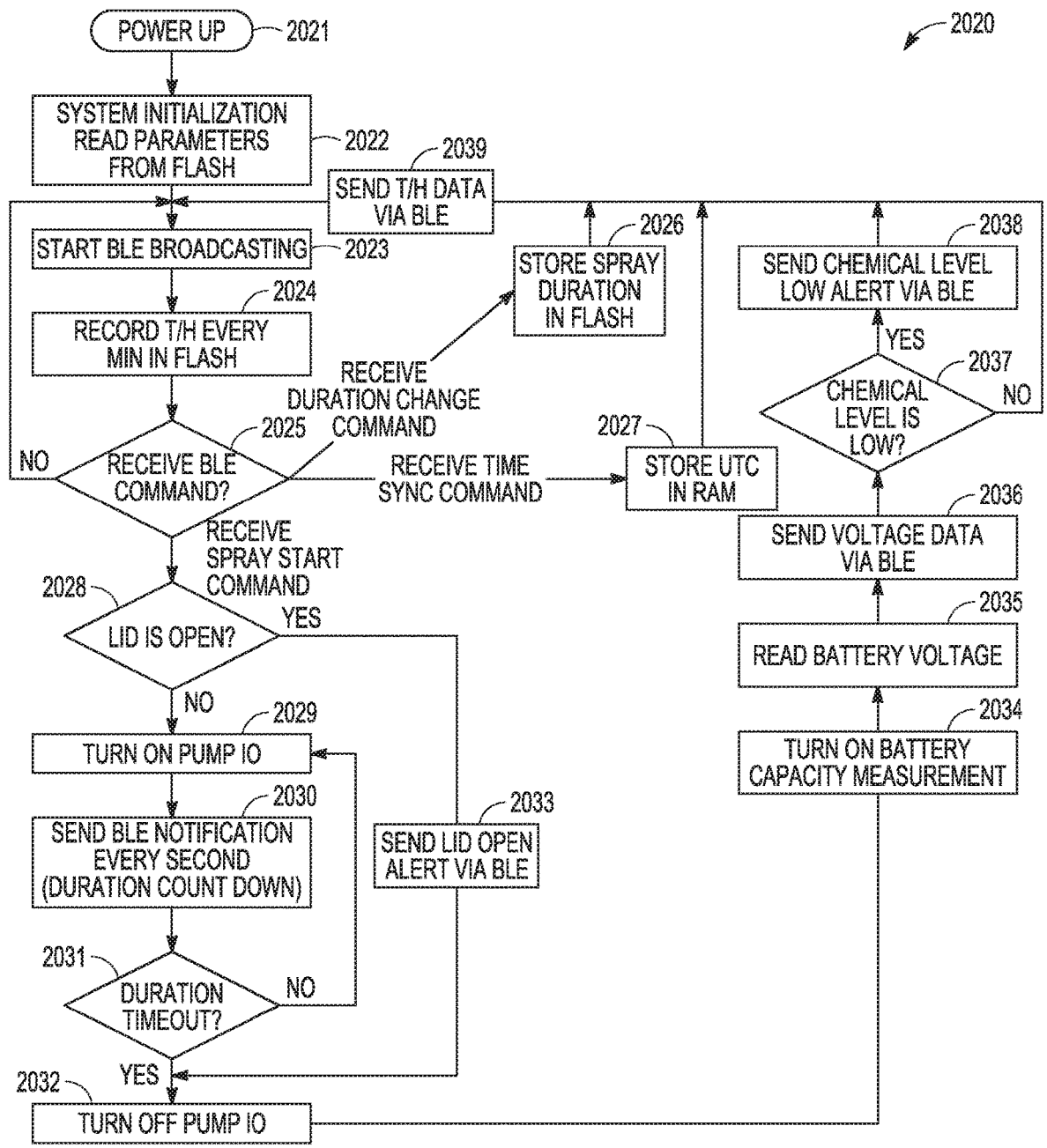
FIG. 20 is a flow chart illustrating an embodiment of another method for controlling conduction of hygiene cycles.

FIG. 20 is a flow chart illustrating an embodiment of a method 2020 for controlling hygiene cycles conducted by a hygiene device attached to a box to be cleaned and/or sanitized, such as hygiene device 1010 attached to box 1001. Method 2020 is similar to method 1900 but uses temperature and/or humidity sensors installed in the box to sense the temperature and/or humidity inside the box. In one embodiment, a control circuit of the hygiene device, such as control circuit 1733, is programmed to perform method 2020. For example, method 2020 can be performed by the control circuit by executing instructions stored in a storage medium of the control circuit as firmware.

At 2021, the control circuit is turned on (powered up). At 2022, a system initialization is performed, during which parameters controlling a hygiene cycle is read from a flash memory of the control circuit. At 2023, BLE broadcasting is started (e.g., via communication link 1021). While a BLE connection is used as an example, any suitable wireless communication technology can be used to establish the wireless connection (e.g., communication link 1021) needed for performing method 2020.

At 2024, readings from the temperature and/or humidity (T/H) sensors are recorded in the flash memory periodically (e.g., with a period specified in minutes). At 2025, whether a command is received via the BLE connection is checked. At 2026, if a duration change command specifying a spray duration for the hygiene cycle is received via the BLE connection, the received spray duration is stored in the flash memory for use in the current and subsequent hygiene cycles. At 2027, if a time sync command with UTC (a time specified in UTC) is received via the BLE connection, the received UTC is stored in a RAM of the control circuit.

At 2028, if a spray start command is received via the BLE connection, whether the lid of the box is open is checked. At 2029, if the lid is not open, a pump input/output (IO) is turned on. At 2030, a notification that the pump 10 is on is sent out (e.g., to provider API module 1072) via the BLE connection periodically (e.g., every second) as a spray duration countdown. At 2031, whether the spray duration has expired is checked. If the spray duration has not expired, the pump IO stays on. At 2032, if the spray duration has expired, the pump IO is turned off. At 2033, if the lid is open at 2028, a lid-open alert is sent out (e.g., to provider API module 1072) via the BLE connection, and the pump 10 stays off.

At 2034, a battery capacity measurement is started for measuring the status of a battery of the hygiene device (e.g., battery 1734). At 2035, voltage of the battery is read. At

2036, the voltage of the battery as an indication of the status of the battery (e.g., which indicates whether the battery needs to be recharged or replaced) is sent out (e.g., to provider API module 1072) via the BLE connection. At 2037, whether a chemical level (i.e., the level of the hygiene agent in a container unit such as container unit 1611) is checked. At 2038, if the chemical level is low (e.g., falling below a specified threshold level), a chemical-level-low alert is sent out (e.g., to provider API module 1072) via the BLE connection. At 2039, readings from the T/H sensors are sent out (e.g., to provider API module 1072) via the BLE connection.

In various embodiments, once the system initialization is performed at 2022, steps 2023-2039 repeat according to the parameters read from the flash memory until the control circuit is turned off (powered down). In various embodiments, the control circuit is turned on and off when the hygiene device is turned on and off.

Figure 21:
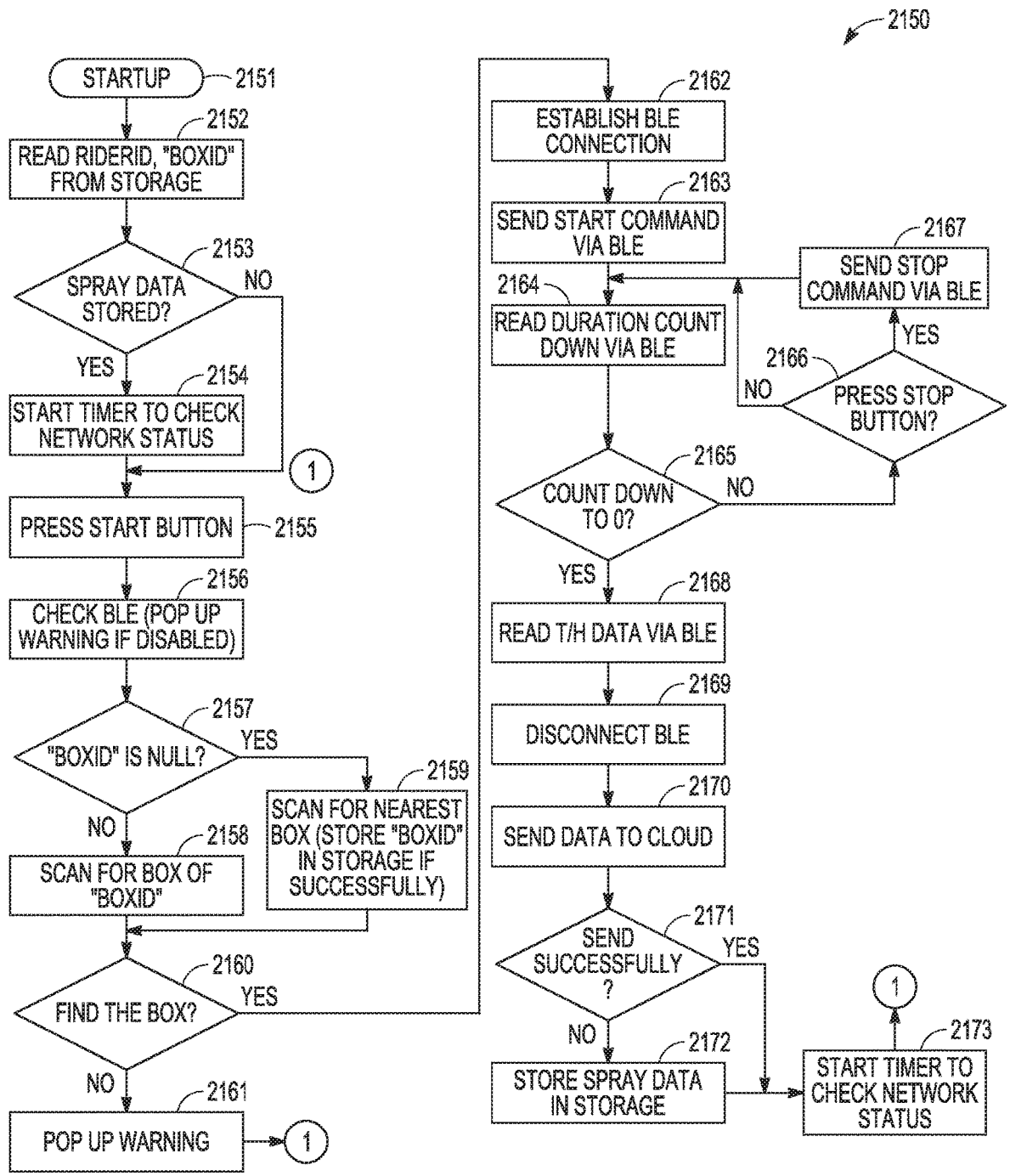
FIG. 21 is a flow chart illustrating an embodiment of a method for operating a user interface device of the system of FIG. 10.

FIG. 21 is a flow chart illustrating an embodiment of a method 2150 for operating a user interface device, such as user interface device 1020, that is used by the user participating in conduction of a hygiene cycle using a hygiene device attached to a box to be cleaned and/or sanitized, such as hygiene device 1010 attached to box 1001. Method 2150 can be performed by a software application installed in the user interface device. In one embodiment in which the user interface device is a mobile device such as a smartphone, an application is installed in the mobile device to perform method 2150. In one embodiment, provider API module 1072 is configured to perform method 2150.

At 2151, the application is started. At 2152, a rider identification (riderID) and a box identification (boxID) are read from a storage device of the user interface device. The riderID is an identification code assigned to the user such as a food delivery rider. The boxID is an identification code assigned to the box for which the user (rider) is responsible.

Figure 22:
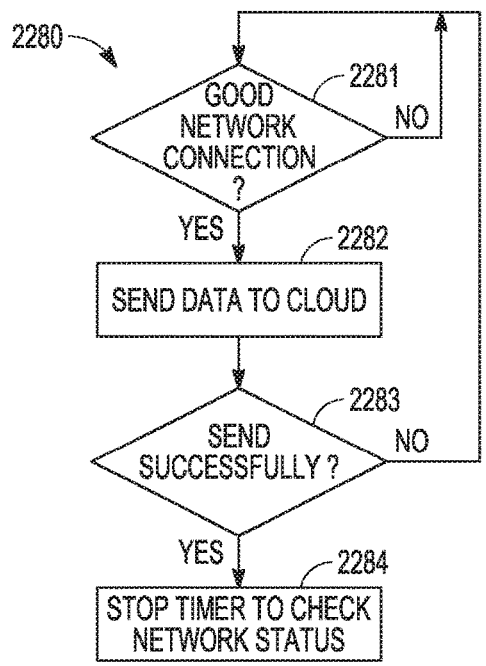
FIG. 22 is a flow chart illustrating an embodiment of a method for checking network status as part of the method of FIG. 21.

At 2153, whether spray data (data needed for conducting the hygiene cycle) are stored in the storage device is checked. At 2154, if the spray data are stored, a timer to check network status is started. At 2155, checking of network status is started (e.g., by pressing a start button). If the spray data are stored, the network status is checked immediately. A method for running the timer for checking network status (the circled "1" in FIG. 21) is illustrated in FIG. 22.

At 2156, whether BLE communication (or any other wireless communication available for use to communicate with the control circuit of the hygiene device) is enabled for the user interface device is checked, and a warning is generated (e.g., by popping up a warning message on a screen of the user interface device) if the BLE communication is disabled.

At 2157, whether the boxID is null (i.e., no boxID was stored in the user interface device and hence read by the application) is checked. At 2158, if the boxID is not null, the box with the boxID is scanned (searched for). At 2159, if the boxID is null, the nearest box is scanned (searched for), and if a box is found, its boxID is stored in the storage device of the user interface device. At 2160, whether the box is found as a result of the scanning at 2158 or 2159 is checked (or confirmed). At 2161, if the box is not found, a warning is generated (e.g., by popping up a warning message on the screen of the user interface device), and the network status is to be checked.

At 2162, the BLE (or another available wireless communication) connection (e.g., communication link 1021) is established. At 2163, a start command is sent to the hygiene device via the BLE connection. At 2164, the spray duration countdown (from step 1908 of method 1900 or step 2030 of method 2020) is read via the BLE connection. At 2165, whether the spray duration countdown has reached 0 is checked. At 2166, if the spray duration countdown has not reached 0, whether a manual stop is performed (e.g., by the user pressing a manual stop button on the user interface device) is checked. At 2167, if the manual stop is performed, a stop command is sent to the control circuit of the hygiene device to stop the spray duration and hence the spray of the hygiene agent.

At 2168, data representing readings from the T/H sensors are read from the control circuit of the hygiene device via the BLE connection. At 2169, the BLE connection is disconnected (i.e., the communication with the hygiene device is stopped at conclusion of the hygiene cycle in the hygiene device). At 2170, data collected from the conduction of the hygiene cycle (including the T/H data and other data related to the performance of the hygiene cycle) are send to a network ("cloud") such as provider's network 1022A. At 2171, whether the data have been successfully sent at 2170 is checked. At 2172, if the data have not been successfully sent, the data are stored in the storage device of the user interface device. At 2173, regardless of whether the data have been successfully sent, the timer to check network status is started.

FIG. 22 is a flow chart illustrating an embodiment of a method 2280 for checking network status as part of method 2150 (the circled "1" in FIG. 21). At 2280, whether there is a good network connection between the user interface device and the network (e.g., the communication link 1023A) is checked. Step 2280 repeats until the good network connection is established. At 2282, if there is a good network connection, data are sent via this network connection. At 2283, whether the data are successfully sent via the network connection is checked. If the data are not successfully sent, checking for the good network connection at 2281 continues. At 2284, if the data are successfully sent, the timer to check network status is stopped. In various embodiments, method 2280 is performed to ensure that data to be sent to the network are successfully sent when a good network connection is available.

Figure 23:
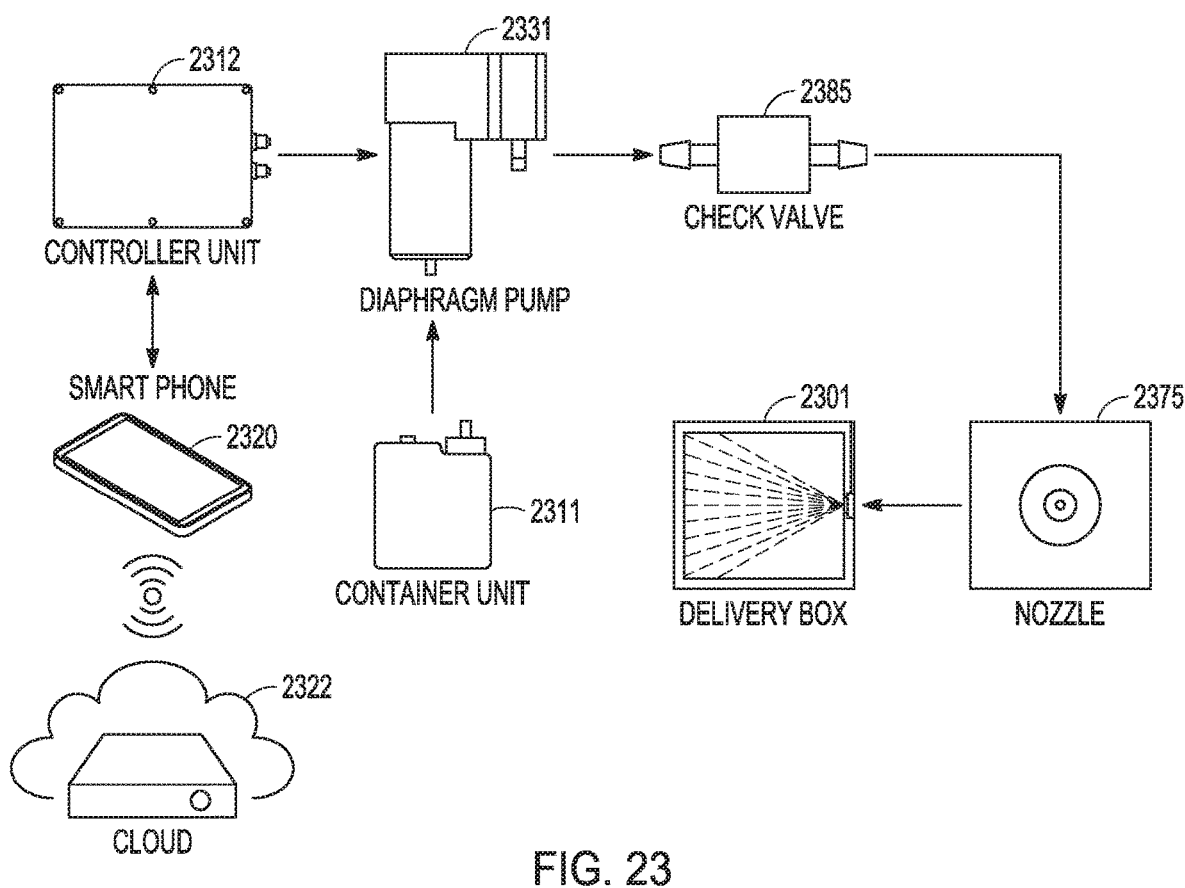
FIG. 23 is a block diagram illustrating an embodiment of a controller unit of a hygiene device as used in a system for cleaning and sanitizing a box, such as the system of FIG. 10.
Figure 24:
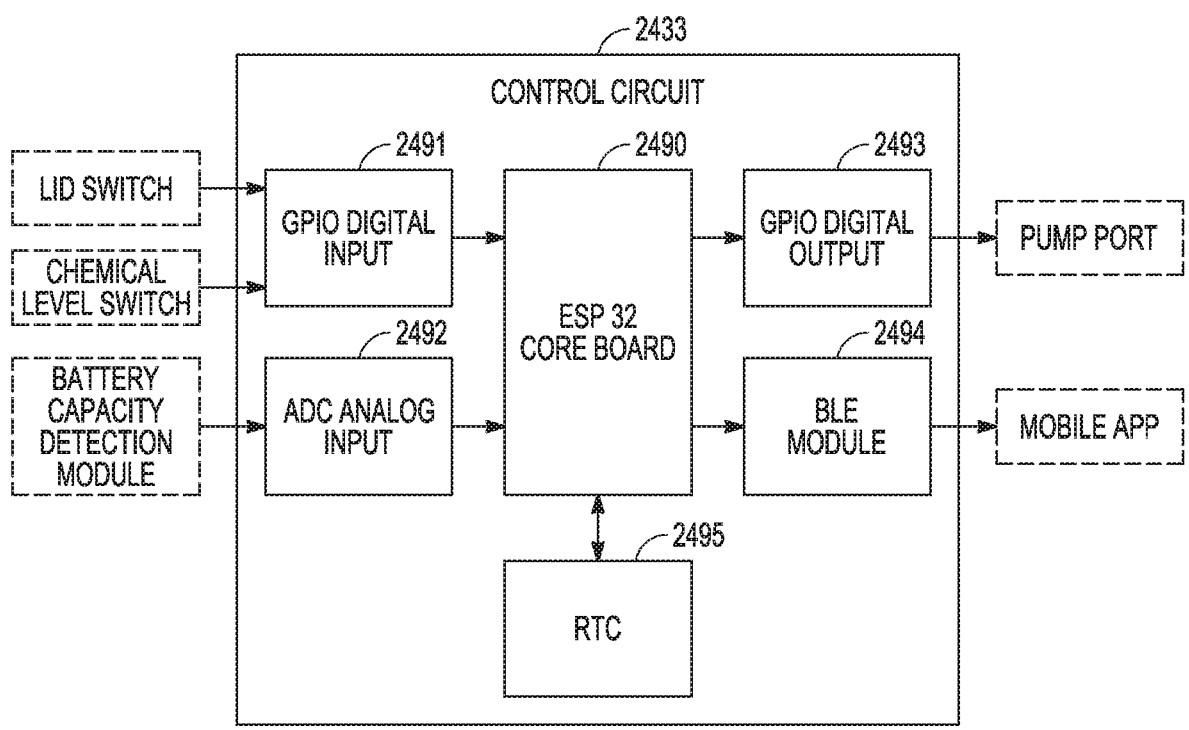
FIG. 24 is a block diagram illustrating an embodiment of a control circuit of the controller unit of FIG. 23.
Figure 25:
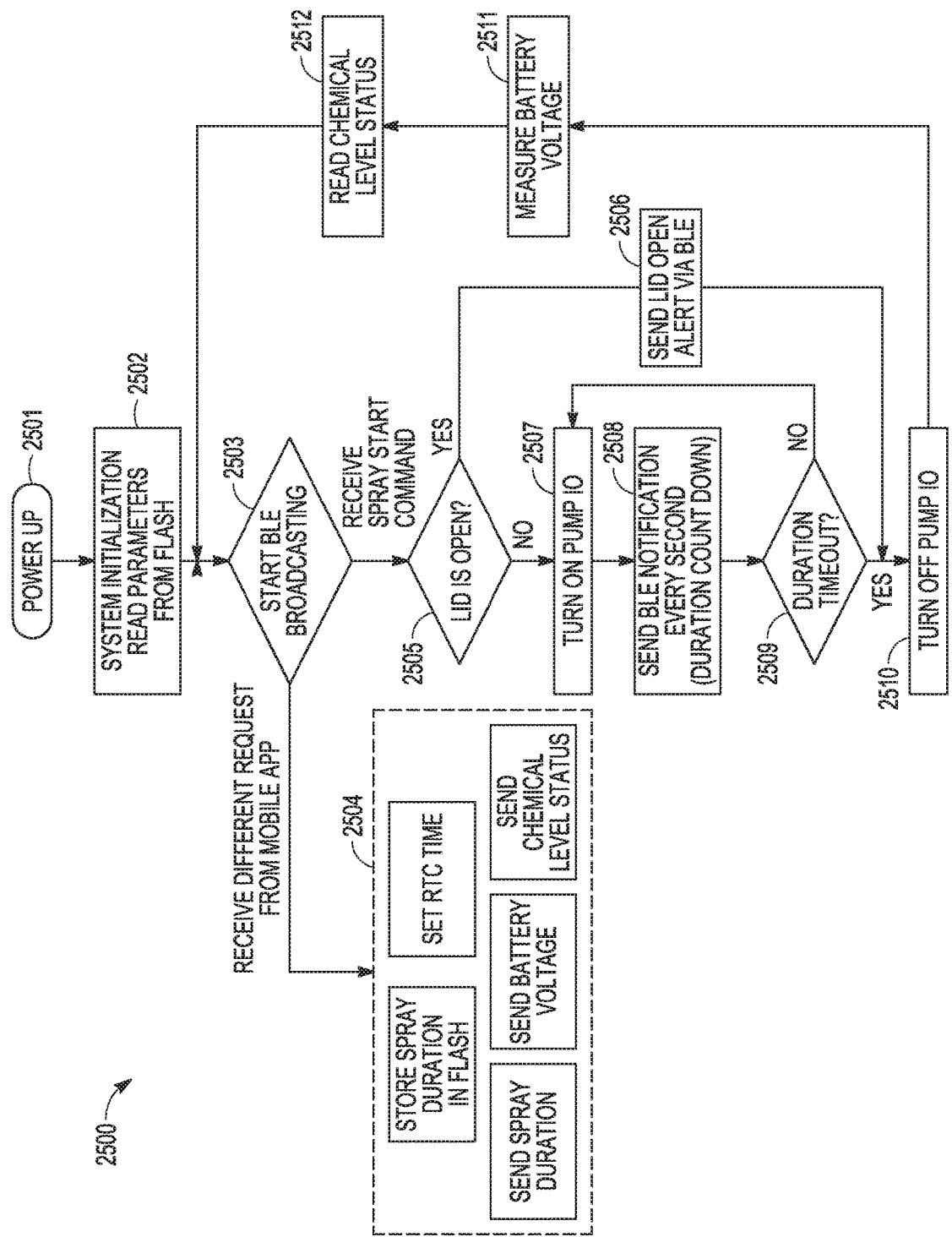
FIG. 25 is a flow chart illustrating an embodiment of operation of the control circuit of FIG. 24.

FIGS. 23-25 illustrate an embodiment of a controller unit 2312 of a hygiene device (e.g., hygiene device 1010) in a system (e.g., system 1000) for cleaning and/or sanitizing a box (e.g., box 1001), including its circuit and operations. In various embodiments, the controller unit includes a control circuit installed with firmware configured to communicate with a user interface device (e.g., user interface device 1020), such as a mobile device (e.g., a smart phone), installed with a user application. The user application can connect with the firmware for controlling performance of the hygiene cycles and acquiring information regarding the performance. In various embodiments, the provider of system 1000 provides the user with an SDK allowing the user to develop the user application.

FIG. 23 is a block diagram illustrating an embodiment of controller unit 2312. The illustrated system can represent examples of various components of system 1000 as well as the box to be cleaned and/or sanitized using system 1000, and includes:

Controller unit 2312 (which can represent an example of controller unit 1612);
Cloud 2322 (which can represent an example of provider network 1022A and/or a user network 1022B);
Smart Phone 2320 (which can represent an example of user interface device 1020);

Pump 2331 (which can represent an example of pump 1731);

Container Unit 2311 (which can represent an example of container unit 1611);

Check valve 2385 (which can represent an example of check valve 1785);

Nozzle 2375 (which can represent an example of nozzles 1475); and

Delivery box 2301 (which can represent an example of box 1001).

In various embodiments, controller unit 2312 can communicate with smart phone 2320 and communicate with cloud 2322 (directly and/or via smart phone 2320) to receive commands controlling conduction of the hygiene cycles for clearing and sanitizing delivery box 2301, and can communicate with pump 2331 and container unit 2311 for conducting the hygiene cycles by pumping the hygiene agent to nozzle 2375 through check valve 2385. When used in and with system 1000, the illustrated system can operate as discussed above, with reference to FIGS. 10-22, for system 1000.

FIG. 24 is a block diagram illustrating an embodiment of a control circuit 2433 of controller unit 2312. Control circuit 2433 can represent an example of control circuit 1733. In the illustrated embodiment, control circuit 2433 includes a core board 2490 (based on an ESP 32 microcontroller), a digital input 2491 (general-purpose input/output), an analog input 2492 (analog-to-digital converter), a digital output 2493 (general-purpose input/output), a BLE module 2494 (wireless communication circuit using BLE technology), and a real time clock (RTC) 2495. Using firmware, the core board 2490 can be configured to perform the various functions of control circuit 2433 related to the control of the hygiene cycles as discussed in this document (including functions of control circuits 233, 633, 733, and 1733). Some examples of such functions include:

BLE communication with mobile application via BLE module 2494;

BLE command to trigger spray via digital output 2493 and a pump port;

Detection of battery capacity via analog input 2493 and a battery capacity detection module;

Detection of lid switch state via digital input 2491;

Detection of chemical level via digital input 2491 and a chemical level switch; and Tracking times of various events via RTC 2495.

FIG. 25 is a flow chart illustrating an embodiment of a method 2500 performed using control circuit 2433. In various embodiments, the firmware installed in core board 2490 supports the operation of control circuit 2433 including performance of method 2500.

At 2501, control circuit 2433 is turned on (powered up). At 2502, a system initialization is performed, during which parameters controlling a hygiene cycle is read from a flash memory of control circuit 2433. At 2503, BLE broadcasting is started (e.g., via BLE module 2494). While a BLE connection is used as an example, any suitable wireless communication technology can be used to establish the wireless connection needed for performing method 2500.

At 2504, if one of various requests is receive from the mobile application, the request is responded. Examples of such responses include storing the spray duration into the flash memory, setting time of RTC 2495, sending spray duration to the hygiene device, sending battery voltage to the mobile application, and sending chemical level (level of the hygiene agent) to the mobile application.

At 2505, if a spray start command is received via BLE module 2494, whether the lid of the box is open is checked. At 2507, if the lid is not open, a pump input/output (IO) is turned on. At 2508, a notification that the pump IO is on is sent the mobile application via BLE module 2494 periodically (e.g., every second) as a spray duration countdown. At 2509, whether the spray duration has expired is checked. If the spray duration has not expired, the pump IO stays on. At 2510, if the spray duration has expired, the pump IO is turned off. At 2506, if the lid is open at 2505, a lid-open alert is sent to the mobile application via BLE module 2494, and the pump IO stays off.

At 2511, a battery voltage is measured for battery of the hygiene device (e.g., battery 1734). At 2512, a chemical level status (i.e., the level of the hygiene agent in a container unit such as container unit 1611) is read.

In various embodiments, once the system initialization is performed at 2502, steps 2503-2512 repeat according to the parameters read from the flash memory until the control circuit is turned off (powered down). In various embodiments, the control circuit is turned on and off when the hygiene device is turned on and off.

In various embodiments, an SDK, which can take the form of an API in a mobile device (e.g., provider API module 1072 in user interface device 1020) is provided to users of a hygiene system, such as system 1000, or any system developed using the present subject matter for cleaning and/or sanitizing food delivery boxes or other containers, by the provider of the hygiene system. The SDK can be used, for example, to develop an application to be installed in smart phone 2320 and connecting to the firmware of control circuit 2433. The users can use the SDK to develop their own mobile applications for controlling the hygiene cycles through the control circuit. Examples of requirements for such an SDK are discussed below, with "the Application" referring to a mobile application that can be developed using the SDK for connecting with control circuit 2433. In various embodiments, provider API module 1072 can be configured to allow the Application to perform various functions specified as the following requirements for the SDK. While control circuit 2433 is used as an example of the control circuit called by the Application for controlling the hygiene cycles, the Application is not limited to use with control circuit 2433 but can call any control circuit capable of controlling the hygiene cycles according to the present subject matter.

The Application can execute a hygiene cycle (e.g., the hygiene cycle as discussed in this document). The Application can call control circuit 2433 and provide memory addresses to store returned values such as spray status, battery level, lid open alarm, and/or error type. In various embodiments, for the Application to execute the hygiene cycle under normal circumstances, the SDK can, for example:

transmit a cycle start command via BLE (or any other suitable wireless communication) to control circuit 2433 to start the hygiene cycle;

receive the spray status from control circuit 2433 via BLE;

receive the battery level from control circuit 2433 via BLE;

receive the lid open alarm from control circuit 2433 via BLE;

transmit device identification (e.g., identifying the box to be cleaned and/or sanitized), time stamp of the hygiene cycle, pumping time (the time interval during which the hygiene agent is pumped to spray), battery level, the lid open alarm, etc., to the provider's network (e.g., provider's network 1022A) at the end of the hygiene cycle;

get current UTC from the provider's network and write to control circuit 2433 via BLE;

sync up with the provider's network on the pumping time setting, and if there is any change made within the provider's network, push the new value to control circuit 2433;

check the provider's network for any software update, push the latest software package to the mobile device (e.g., user interface device 1020); and return error value to indicate the type of error if any error occurs (e.g., BLE communication error and timeout error).

The criteria for meeting these SDK requirements include:

in the memory address provided, the value of the spray status, the battery level, the lid open alarm, and the error type are updated;

data intended to be sent to the provider's network is sent to the provider's network;

updated pumping time setting on the provider's network, if any, is pushed to control circuit 2433; and software update from the provider's network, if any, is pushed to the mobile device.

The Application can initiate and lock down the BLE connection. The Application can call control circuit 2433 and provide it with the BLE device identification by interpreting the quick response (QR) code it scanned (e.g., from the box to be cleaned and/or sanitized). In various embodiments, for the Application to initiate and lock down the BLE connection, the SDK can, for example:

start scanning BLE devices (e.g., all the devices capable of connecting to the Application via BLE and within the BLE range, including all the hygiene devices within the BLE range) and connect to the one whose identification matches the one provided by the Application;

lock down this BLE (hygiene) device to ensure connection to the same device throughout the BLE communication; and return value indicating whether the connection is successful or failed. The criteria for meeting these SDK requirements include that the Application connects to the right BLE device (e.g., the targeted hygiene device).

The Application can set the pump-on time (or spray time). The Application can call control circuit 2433 and provide it with the value of time in second (e.g., 3 seconds or 10 seconds). In various embodiments, to set the pump-on time, the Application can:

write the pumping time value into control circuit 2433 via BLE; and return value indicating whether the setting change is successful or failed.

The criteria for meeting these SDK requirements include that the new time is updated in control circuit 2433 register.

The Application can execute an emergency stop. The Application can call control circuit 2433 to execute the emergency stop. In various embodiments, for the Application to execute the emergency stop, the SDK can:

transmit the stop command immediately to control circuit 2433 via BLE; and retransmit the command, if a returning value indicates failure or error, until the pumping or spraying is stopped or the end of the normal cycle.

The criteria for meeting these SDK requirements include that the pumping or spraying of the hygiene agent is immediately stopped after the stop command is executed.

The Application can generate a cycle start reminder. The Application can call control circuit 2433 to get the time stamp of the next hygiene cycle. In various embodiments, for the Application to generate a cycle start reminder, the SDK can, for example, retrieve the schedule from the provider's network and return the time information to the Application. The criteria for meeting this SDK requirements include that the schedule information is passed on to the Application.

In various embodiments, the SDK meeting the requirements including those discussed above can be configured and used for performing, for example, any one or any combination of the following functions in using a hygiene system (e.g., hygiene system 100 or 1000) for a food delivery box (e.g., box 101 or 1001, as being used for food delivery):

Information push: the provider can push provider information including product manual, operation manual, training materials, standard operating procedure, video, and/or other materials to the users by using the SDK;

User supervision: the provider can use the SDK to supervise the users and ensure that the provider's products (or products authorized by the provider, e.g., the hygiene agent) are used, the correct products are used, and the products are used according to the provider's instructions or suggestions.

Behavior analysis: the provider can analyze behavior of the users (including behavior of a single user and/or a group of users) with information collected using the SDK (e.g., working area, working hours, workload, location, and/or cleaning and sanitizing habits);

Performance review: performance of the users can be evaluated using record of hygiene cycles completed (e.g., for rewarding those with high completion rates and/or penalizing those with low completion rates), by using the SDK;

Inventory management: product (e.g., hygiene agent) inventory can be monitored for online product ordering, consumption summary, and/or ordering notification, by using the SDK;

Hygiene system status monitoring: various operational status of the hygiene system (e.g., equipment status, failure detection, bug fixing procedure, lift time prediction, battery level display and notification, and/or chemical refill notification) can be monitored using the SDK;

Remote connection: the SDK can allow for remote monitoring, operating, fixing, upgrading, and/or disabling the hygiene system;

User feedback: the SDK can transmit feedback from the users (e.g., information about equipment failure and/or suggestion for improvement) to the provider;

Sensing: the SDK can acquire information related to content of the food delivery box and/or its environment (e.g., using one or more sensors installed in or on the food delivery box to sense whether there are unintended contents and/or to sense weather conditions);

Interaction with other applications: the SDK can interact with other mobile application software installed in the same user interface device (e.g., the mobile device) such as a calendar or social media applications such as WeChat, Facebook, and/or Twitter;

Safety: alarms can be sent to the provider and/or presented to the user using the SDK when a safety concern is raised (e.g., the user is far away from the food delivery box with its lid open and/or when an acceleration sensor installed in or on the food delivery box detects violent movements of the food delivery box);

Hygiene cycle performance assurance: hygiene-related information can be sensed using one or more sensors (e.g., thermometer, humidity sensor, odor sensor, and/or camera) installed in or on the food delivery box and analyzed by the SDK to evaluate performance of the hygiene cycles (e.g., the hygiene cycles as discussed in this document), such as to ensure satisfactory hygiene cycle performance and/or to allow for optimization of the hygiene cycle performance;

Information to the users: the SDK can transmit notification to the users (e.g., weather and/or other environmental information related to food delivery);

Interlock to delivery ordering: the SDK can connect to the Application to learn food ordering and delivery status to forbid initiation of a hygiene cycle when there is an outstanding order for which the delivery is not completed, to suggest for initiation of a hygiene cycle when there is no outstanding order, and/or to optimizing a hygiene strategy (e.g., schedule for conducting the hygiene cycles) based on each user's workload as automatically learned by the SDK;

User identification: the SDK can allow access to the Application using voice recognition and/or facial recognition to ensure only an authorized user can operation the hygiene system using the Application; and Multi-level authority: the SDK can include functions that are accessible by the users depending on their authority, such that functions of the SDK in different user interface devices (e.g., the mobile devices) can have different levels of accessibility corresponding to different levels of authority given to their users.

These functions and requirements of the SDK and the Application developed using the SDK, as well as the functions or tasks that can be performed using the SDK, are presented by way of example but not by way of limitation. In various embodiments, one or more subsets of such functions and requirements can be applied, and one or more new functions and requirements can be added, by those skilled in the art upon reading and understanding this document. In various embodiments, the provider and/or the users can implement additional functions and tasks using the functions of the SDK as discussed in this document.

Some non-limiting examples (Examples 1-92) of the present subject matter are provided as follows:

In Example 1, a system for cleaning and sanitizing a box configured to be carried by a user may include a hygiene device. The hygiene device may be configured to be attached to the box, and may include an agent container configured to contain a hygiene agent, a spray nozzle configured to be inserted into the box (or otherwise placed in the box to perform its function), a pump in fluid communication with the agent container and in fluid communication with the spray nozzle, and a control circuit. The pump may be configured to pump the hygiene agent through the spray nozzle to produce a mist of the hygiene agent in the box. The control circuit may be configured to control hygiene cycles and may include a communication circuit configured to transmit and receive information, a hygiene cycle management circuit configured to initiate each cycle of the hygiene cycles, and a monitoring circuit configured to record information related to performance of each cycle of the hygiene cycles and to transmit the recorded information out of the hygiene device through the communication circuit.

In Example 2, the subject matter of Example 1 may optionally be configured such that the hygiene agent includes a cleaning agent.

In Example 3, the subject matter of Example 1 may optionally be configured such that the hygiene agent includes a sanitization agent.

In Example 4, the subject matter of Example 1 may optionally be configured such that the hygiene agent includes a cleaning and sanitization agent.

In Example 5, the subject matter of any one or any combination of Examples 1 to 4 may optionally be configured such that the hygiene cycle management circuit is further configured to control the pumping of the hygiene agent during each cycle of the hygiene cycles.

In Example 6, the subject matter of Example 5 may optionally be configured such that the hygiene cycle management circuit is configured to time the pumping of the hygiene agent and end the pumping of the hygiene agent when a specified time interval expires.

In Example 7, the subject matter of any one or any combination of Examples 1 to 6 may optionally be configured to further include a power source including one or more batteries.

In Example 8, the subject matter of Example 1 may optionally be configured such that the control circuit further includes a power management circuit coupled to the power source to monitor for a need to replace or recharging the one or more batteries.

In Example 9, the subject matter of any one or any combination of Examples 1 to 8 may optionally be configured to further include the box being a portable food delivery box.

In Example 10, the subject matter of any one or any combination of Examples 1 to 9 may optionally be configured such that the box has a flat bottom, and the spray nozzle is configured to be incorporated into a center of the bottom.

In Example 11, the subject matter of Example 10 may optionally be configured such that the box is a rectangular box having the flat bottom, a flat lid, four flat sides each coupled between the flat bottom and the flat lid when the lid is closed. The box includes one or more hinges connecting between the lid and one side of the four sides and a locking mechanism configured to lock the lid in a closed position.

In Example 12, the subject matter of any one or any combination of Examples 1 to 11 may optionally be configured such that the hygiene device is configured to be detachably attached to the box.

In Example 13, the subject matter of Example 12 may optionally be configured such that the hygiene device includes a container unit including the agent container, a controller unit including the diaphragm pump, the control circuit, and a battery, tubing coupled between the container and the controller box to provide for the fluid communication between the agent container and the pump, and tubing between the controller unit and the spray nozzle to provide for the fluid communication between the pump and the spray nozzle. The container unit and the controller unit are each configured to be detachably attached to the box.

In Example 14, the subject matter of any one or any combination of Examples 1 to 13 may optionally be configured such that the agent container includes a refillable bottle.

In Example 15, the subject matter of any one or any combination of Examples 1 to 14 may optionally be configured such that the hygiene cycle management circuit is configured to initiate the hygiene cycles according to a specified schedule.

In Example 16, the subject matter of Example 15 may optionally be configured such that the hygiene cycle management circuit is configured to initiate the hygiene cycles periodically.

In Example 17, the subject matter of any one or any combination of Examples 1 to 16 may optionally be configured such that the hygiene cycle management circuit is configured to initiate each cycle of the hygiene cycles in response to a user command.

In Example 18, the subject matter of Example 17 may optionally be configured such that the hygiene cycle management circuit is configured to receive the user command through the communication circuit.

In Example 19, the subject matter of any one or any combination of Examples 11 to 18 may optionally be configured such that the hygiene cycle management circuit is configured to confirm that the box is empty and that the lid is closed and to start spraying a hygiene agent upon the confirmation.

In Example 20, the subject matter of Example 19 may optionally be configured such that the hygiene cycle management circuit is configured to transmit a confirmation request signal for confirming that the box is empty and that the lid is closed, to receive a confirmation response signal confirming in response to the transmission of the confirmation request signal, and to cause the spray nozzle and the pump to start spraying the hygiene agent upon receiving the confirmation response signal.

In Example 21, the subject matter of any one or any combination of Examples 1 to 20 may optionally be configured such that the monitoring circuit is further configured to notify the user the status of each hygiene cycle of the hygiene In Example 22, the subject matter of Example 21 may optionally be configured such that the monitoring circuit is further configured to notify the user to perform one or more functions during each hygiene cycle of the hygiene cycles according to a hygiene procedure.

In Example 23, the subject matter of any one or any combination of Examples 1 to 22 may optionally be configured such that the monitoring circuit is configured to record information including one or more of information identifying the box, information identifying the user, and timing information for each hygiene cycle of the hygiene cycles.

In Example 24, the subject matter of any one or any combination of Examples 1 to 23 may optionally be configured such that the monitoring circuit is configured to transmit the recorded information out of the hygiene device using wireless communication technology.

In Example 25, the subject matter of any one or any combination of Examples 1 to 24 may optionally be configured to further include a user interface device configured to present information related to each cycle of the hygiene cycles to the user and receive information related to each cycle from the user.

In Example 26, the subject matter of Example 25 may optionally be configured such that the user interface device includes a mobile device.

In Example 27, the subject matter of Example 26 may optionally be configured such that the mobile device includes a cellphone and a hygiene application installed on the cellphone. The hygiene application allows the user to participate in control of each cycle of the hygiene cycles.

In Example 28, the subject matter of any one or any combination of Examples 25 to 27 may optionally be configured such that the user interface device is configured to allow the user to initiate a cycle of the hygiene cycles.

In Example 29, the subject matter of any one or any combination of Examples 25 to 27 may optionally be configured such that the user interface device is configured to allow the user to start spraying of the hygiene agent during each cycle of the hygiene cycles.

In Example 30, the subject matter of any one or any combination of Examples 25 to 29 may optionally be configured such that the user interface device is configured to receive the recorded information from the hygiene circuit.

In Example 31, the subject matter of Example 30 may optionally be configured to further include an analysis center configured to be communicatively coupled to the user interface device via wireless communication and to analyze the recorded information and produce feedback information based on an outcome of the analysis. The user interface device is configured to relay the recorded information to the analysis center and to receive the feedback information from the analysis center.

In Example 32, a method for cleaning and sanitizing a box configured to be carried by a user is provided. The method may include verifying emptiness of the box, starting an automatic hygiene cycle using a battery-powered portable hygiene device attached to the box, recording information related to performance of the hygiene cycle, and transmitting the recorded information to an analysis center for analysis and monitoring of hygiene status of the box.

In Example 33, the subject matter of starting the hygiene cycle as found in Example 32 may optionally include spraying a hygiene agent into the box to produce a mist of the hygiene agent in the box to result in substantially uniform distribution of the hygiene agent on interior surfaces of the box.

In Example 34, the subject matter of spraying the hygiene agent as found in Example 33 may optionally include spraying a cleaning agent.

In Example 35, the subject matter of spraying the hygiene agent as found in Example 33 may optionally include spraying a sanitization agent.

In Example 36, the subject matter of spraying the hygiene agent as found in Example 33 may optionally include spraying a cleaning and sanitization agent.

In Example 37, the subject matter of spraying the hygiene agent into the box as found in Example 33 may optionally include spraying the hygiene agent into the box using a single nozzle positioned at a bottom of the box.

In Example 38, the subject matter of any one or any combination of Examples 32 to 37 may optionally further include using a user interface device to communicate with the user regarding the hygiene cycle.

In Example 39, the subject matter of using the user interface device as found in Example 38 may optionally include using a cellphone carried by the user.

In Example 40, the subject matter of transmitting the recorded information to the analysis center as found in any one or any combination of Examples 38 and 39 may optionally further include transmitting the recorded information through a network using a wireless communication technology.

In Example 41, the subject matter of Example 40 may optionally further include producing instructions for the user based on the analysis and monitoring of hygiene status of the box and presenting the instruction for the user using the user interface device.

In Example 42, the subject matter of any one or any combination of Examples 38 to 41 may optionally further include verifying emptiness of the box includes instructing the user to verify that the box is free of solid or liquid waste resulting from food delivery. The box is a food delivery box.

In Example 43, the subject matter of verifying emptiness of the box as found in Example 38 may optionally include instructing the user to verify the emptiness of the box.

In Example 44, the subject matter of starting the automatic hygiene cycle as found in any one or any combination of Examples 38 to 43 may optionally include starting the automatic hygiene cycle in response to a command transmitted from the application upon verification that the box is empty.

In Example 45, the subject matter of starting the automatic hygiene cycle as found in Example 34 may optionally include starting the automatic hygiene cycle according to a specified schedule and upon verification that the box is empty.

In Example 46, the subject matter of starting the automatic hygiene cycle as found in Example 45 may optionally include starting the automatic hygiene cycle on a periodic basis and upon verification that the box is empty.

In Example 47, the subject matter of any one or any combination of Examples 33 to 46 may optionally further include starting, timing, and ending the spray of the hygiene according to a specified time interval.

In Example 48, the subject matter of Example 47 may optionally further include using the user interface device to instruct the user to dry interior surfaces of the box upon completion of the hygiene cycle.

In Example 49, the subject matter of any one or any combination of Examples 33 to 46 may optionally further include using the user interface device to instruct the user to dry interior surfaces of the box upon completion of the hygiene cycle.

In Example 50, the subject matter of any one or any combination of Examples 33 to 49 may optionally further include using the user interface device to instruct the user to clean exterior surfaces of the box periodically.

In Example 51, a system for cleaning and sanitizing a box configured to be carried by a user may include a hygiene device and a user interface device. The hygiene device may be configured to be affixed to the box, to conduct hygiene cycles each including spray of a hygiene agent into the box, to record information related to performance of each cycle of the hygiene cycles, and to transmit the recorded information out of the hygiene device via a wireless communication link. The user interface device may be configured to transmit commands controlling the conduction of the hygiene cycles to the hygiene device via the wireless communication link and to receive the recorded information transmitted from the hygiene device via the wireless communication link.

In Example 52, the subject matter of Example 51 may optionally be configured such that the user interface device includes a mobile device, and to further include an application programming interface module installed in the mobile device to allow for access to the hygiene device by a user application installed in the mobile device. The application programming interface module is configured to transmit the commands controlling the conduction of the hygiene cycles to the hygiene device via the wireless communication link and to receive the recorded information transmitted from the hygiene device via the wireless communication link.

In Example 53, the subject matter of Example 52 may optionally be configured to further include a network, and such that the user interface device is configured to communicate with the network via a wireless network connection, and the application programming interface module is configured to receive one or more first commands of the commands controlling the conduction of the hygiene cycles from the network via the network connection and to transmit the received one or more first commands to the hygiene device via the wireless communication link.

In Example 54, the subject matter of Example 53 may optionally be configured such that the application programming interface module is configured to receive one or more second commands of the commands controlling the conduction of the hygiene cycles from the user application and to transmit the received one or more second commands to the hygiene device via the wireless communication link.

In Example 55, the subject matter of Example 54 may optionally be configured such that the application programming interface module is configured to receive a cycle start command of the one or more other commands from the user application. The cycle start command is received from the user for initiating the conduction of a hygiene cycle of the hygiene cycles.

In Example 56, the subject matter of any one or any combination of Examples 53 to 55 may optionally be configured such that the application programming interface module is configured to receive the recorded information from the hygiene device via the wireless communication link and to transmit at least a portion of the received recorded information to the network.

In Example 57, the subject matter of any one or any combination of Examples 53 to 56 may optionally be configured such that the application programming interface module is configured to receive the recorded information from the hygiene device via the wireless communication link and to transmit at least a portion of the received recorded information to the user application.

In Example 58, the subject matter of any one or any combination of Examples 56 and 57 may optionally be configured such that the hygiene device includes a battery and a control circuit configured to monitor a status of the battery, and the recorded information includes information indicative of the status of the battery.

In Example 59, the subject matter of any one or any combination of Examples 56 to 58 may optionally be configured such that the hygiene device includes a container unit configured to contain the hygiene agent and a control circuit configured to monitor a level of the hygiene agent in the container unit, and the recorded information includes information indicative of the level of the hygiene agent in the container unit.

In Example 60, the subject matter of any one or any combination of Examples 53 to 59 may optionally be configured such that the mobile device includes a cellphone, and the wireless network connection includes at least one of Wi-Fi or a cellular network.

In Example 61, the subject matter of any one or any combination of Examples 51 to 60 may optionally be configured such that the wireless communication link includes a Bluetooth communication link or a Bluetooth Low Energy (BLE) communication link.

In Example 62, a method for cleaning and sanitizing a box configured to be carried by a user is also provided. The method may include conducting hygiene cycles using a hygiene device affixed onto the box, controlling the conduction of each hygiene cycle of the hygiene cycles using a user interface device configured to be carried by the user and to be communicatively coupled to the hygiene device via a wireless communication link, recording information related to performance of each hygiene cycle of the hygiene cycles using the hygiene device, and transmitting the recorded information from the hygiene device to the user interface device.

In Example 63, the subject matter of conducting the hygiene cycles as found in Example 62 may optionally include spraying a hygiene agent into the box during each hygiene cycle of the hygiene cycles.

In Example 64, the subject matter of spraying the hygiene agent as found in Example 63 may optionally include using a plurality of nozzles positioned and oriented within the box to produce a mist of the hygiene agent in the box to result in substantially uniform distribution of the hygiene agent on interior surfaces of the box.

In Example 65, the subject matter of any one or any combination of Examples 62 to 64 may optionally further include allowing the user to initiate each hygiene cycle of the hygiene cycles using the user interface device.

In Example 66, the subject matter of Example 65 may optionally further include automatically timing a spray duration during which the hygiene agent is to be sprayed and allowing the user to manually stop the timing of the spray duration using the user interface device.

In Example 67, the subject matter of using the user interface device as found in any one or any combination of Examples 62 to 66 may optionally include using a mobile device configured to function as the user interface device.

In Example 68, the subject matter of Example 67 may optionally include providing the mobile device with an application programming interface module configured to allow the user to control selected functions of the hygiene device and to receive information selected from the recorded information using a user application installed in the mobile device.

In Example 69, the subject matter of any one or any combination of Examples 62 to 68 may optionally further include establishing a wireless network connection between the user interface device and a network.

In Example 70, the subject matter of Example 69 may optionally further include transmitting at least a first portion of the recorded information from the user interface device to the network via the wireless network connection and transmitting at least a second portion of the recorded information from the application programming interface module to the user application for presenting to the user.

In Example 71, the subject matter of controlling the conduction of each hygiene cycle of the hygiene cycles using the user interface device as found in any one or any combination of Examples 62 to 66 may optionally include receiving one or more first commands from the network using application programming interface module, receiving one or more second commands from the user through the user application and the application programming interface module, and transmitting the one or more first commands and the one or more second commands to the hygiene device using the application programming interface module.

In Example 72, the subject matter of any one or any combination of Examples 69 to 71 may optionally further include using the application programming interface module to receive one or more reminders related to the conduction of the hygiene cycles from the network and to transmit the received one or more reminders to the user application for presenting to the user.

In Example 73, a system for controlling a hygiene device may include a mobile device. The hygiene device may be configured to be affixed to a food delivery box to conduct hygiene cycles each including spray of a hygiene agent into the box and to record information related to performance of the hygiene cycles. The hygiene device may be provided to a user of the box by a provider having a provider's network. The mobile device may be configured to be communicatively coupled to the hygiene device via a first wireless communication link, to transmit commands controlling the conduction of the hygiene cycles to the hygiene device via the first wireless communication link, and to receive the recorded information transmitted from the hygiene device via the first wireless communication link.

In Example 74, the subject matter of Example 73 may optionally be configured such that the mobile device is configured to transmit at least one of a command for starting a hygiene cycle of the hygiene cycles, a command for controlling timing of the spray of the hygiene agent during the started hygiene cycle, a time, or a software upgrade to the hygiene device via the first wireless communication link.

In Example 75, the subject matter of Example 74 may optionally be configured such that the mobile device is configured to receive the command for starting the hygiene cycle from the user.

In Example 76, the subject matter of Example 74 may optionally be configured such that the mobile device is configured to generate the command for starting the hygiene cycle automatically.

In Example 77, the subject matter of any one or any combination of Examples 74 to 76 may optionally be configured such that the mobile device is configured to receive at least one of a status of the started hygiene cycle, a battery level of the hygiene device, or an indication of whether the box is open from the hygiene device via the first wireless communication link.

In Example 78, the subject matter of Example 77 may optionally be configured such that the mobile device is configured to be communicatively coupled to the provider's network via a second wireless communication link and to transmit at least one of the battery level of the hygiene device, the indication of whether the box is open, or data related to performance of the each hygiene cycle to the provider's network via the second wireless communication link.

In Example 79, the subject matter of Example 78 may optionally be configured such that the mobile device is configured to receive at least one of a reminder for starting a hygiene cycle of the hygiene cycles, the command for controlling timing of the spray of the started hygiene agent, the time, or the software upgrade from the provider's network via the second wireless communication link.

In Example 80, the subject matter of Example 79 may optionally be configured such that the mobile device is configured to present at least one of the reminder for starting the hygiene cycle, the status of each hygiene cycle, the battery level of hygiene device, or the indication of whether the box is open to the user.

In Example 81, the subject matter of any one or any combination of Examples 73 to 80 may optionally be configured such that the mobile device includes a smartphone.

In Example 82, a non-transitory machine-readable medium may include instructions, which when executed by a machine, cause the machine to perform a method for controlling a hygiene device. The hygiene device may be affixed to a food delivery box and configured to conduct hygiene cycles each including spray of a hygiene agent into the box and to record information related to performance of the hygiene cycles. The method may include transmitting a cycle start command to the hygiene device via a first wireless communication link and receiving the recorded information from the hygiene device via the first wireless communications link. The cycle start command is to start a hygiene cycle of the hygiene cycles. The recorded information may include at least one of a spray status of the started hygiene cycle, a device identification identifying the box, a time stamp of the started hygiene cycle, a pumping time during which the hygiene agent is pumped to spray, a battery level of the hygiene device, or a lid open alarm indicating that a lid of the hygiene device is open.

In Example 83, the subject matter of Example 82 may optionally be configured such that the method further includes transmitting at least portions of the received recorded information to a provider's network via a second wireless communication link, the provider providing the hygiene device to a user of the box.

In Example 84, the subject matter of Example 83 may optionally be configured such that the method further includes receiving a current universal time coordinated (UTC) from the provider's network via the second wireless network and transmitting the received UTC to the hygiene device.

In Example 85, the subject matter of any one or any combination of Examples 83 to 84 may optionally be configured such that the method further includes updating the pumping time in the hygiene device.

In Example 86, the subject matter of Example 85 may optionally be configured such that the method further includes updating the pumping time in the hygiene device to a new pumping time in the provider's network when the pumping time in the hygiene device differs from the new pumping time in the provider's network.

In Example 87, the subject matter of any one or any combination of Examples 83 to 86 may optionally be configured such that the method further includes checking the provider's network for a software update for the hygiene device, receiving a software package for updating the instructions when the software update is available, and updating the instructions using the received software package.

In Example 88, the subject matter of any one or any combination of Examples 83 to 87 may optionally be configured such that the method further includes detecting an error in data transmission via the first wireless communication link or in operation of the hygiene device and transmitting an error indication to the provider's network in response to a detection of the error, the error indication indicative of a type of the detected error.

In Example 89, the subject matter of any one or any combination of Examples 83 to 88 may optionally be configured such that the method further includes identifying the hygiene device from a plurality of devices based on an identification of the hygiene device and locking down connection with the hygiene device via the first wireless communication link in response to the hygiene device being identified to ensure completion of data transmission to and from the hygiene device.

In Example 90, the subject matter of any one or any combination of Examples 83 to 89 may optionally be configured such that the method further includes transmitting a stop command to the hygiene device to cause an immediate stop of the spray of the hygiene agent into the box.

In Example 91, the subject matter of Example 18 may optionally be configured such that the method further includes receiving a stop indication of whether the spray has been stopped and repeating the transmitting of the stop command and receiving the stop indication until the received indication indicates that the spray has been stopped or until the pumping time ends.

In Example 92, the subject matter of any one or any combination of Examples 83 to 91 may optionally be configured such that the method further includes receiving a hygiene cycle schedule from the provider's network and generating a cycle start reminder for starting a next hygiene cycle of the hygiene cycles.

This application is intended to cover adaptations or variations of the present subject matter. It is to be understood that the above description (including the list of Examples 1-92) is intended to be illustrative, and not restrictive. The scope of the present invention should be determined with reference to the appended claims, along with the full scope of legal equivalents to which such claims are entitled.

What is claimed is:

1. A method for controlling hygiene of a portable box for transportation of deliverable packaged foods, the method comprising:
    transmitting a cycle start command to a portable hygiene device using a mobile device, the hygiene device attached to the box and configured to conduct hygiene cycles and to record information related to performance of the hygiene cycles including a location where each hygiene cycle of the hygiene cycles is performed, the cycle start command starting a hygiene cycle of the hygiene cycles;
    receiving the recorded information from the hygiene device using the mobile device; and
    determining whether the hygiene cycles are conducted in compliance with a hygiene procedure established to ensure food safety using the received recorded information including the locations where the hygiene cycles are performed, including determining a number of food deliveries between two cycles of the conducted hygiene cycles using the locations.

2. The method of claim 1, wherein transmitting the cycle start command comprises transmitting a command starting a hygiene cycle of the hygiene cycles including spraying a hygiene agent in liquid form into the box .

3. The method of claim 2, wherein receiving the recorded information from the hygiene device comprises receiving a spray status of the started hygiene cycle.

4. The method of claim 2, wherein receiving the recorded information from the hygiene device comprises receiving a device identification identifying the box.

5. The method of claim 2, wherein receiving the recorded informationom the hygiene device comprises receiving a time stamp of the started hygiene cycle.

6. The method of claim 2, wherein receiving the recorded information from the hygiene device comprises receiving a pumping time during which the hygiene agent is pumped to spray.

7. The method of claim 2, wherein receiving the recorded information from the hygiene device comprises receiving a battery level of the hygiene device.

8. The method of claim 2, wherein receiving the recorded information from the hygiene device comprises receiving a lid open alarm indicating that a lid of the box is open.

9. The method of claim 2, further comprising transmitting a stop command to the hygiene device from the mobile device in response to a user command received by the mobile device to cause an immediate stop of the spray of the hygiene agent into the box.

10. The method of claim 9, further comprising:
- receiving a stop indication by the mobile device, the stop indication indicating whether the spray has been stopped; and
- repeating the transmitting of the stop command and the receiving the stop indication until the received stop indication indicates that the spray has been stopped or until a pumping time ends.

11. The method of claim 1, further comprising transmitting at least portions of the received recorded information from the mobile device to a provider's network, the provider providing a user of the box with technology for the hygiene of the box.

12. The method of claim 11, further comprising updating a pumping time in the hygiene device when the pumping time in the hygiene device differs from a new pumping time in the provider's network, the pumping time being a time interval during which a hygiene agent is pumped to spray into the box for each of the hygiene cycles.

13. The method of claim 11, further comprising:
- checking the provider's network for a software update for the hygiene device;
- receiving a software package for the software update using the mobile device when the software update is available; and
- applying the software update to the hygiene device using the received software package.

14. The method of claim 11, further comprising:
- receiving a hygiene cycle schedule from the provider's network using the mobile device; and
- generating a cycle start reminder for starting a next hygiene cycle of the hygiene cycles using the mobile device.

15. The method of claim 1, further comprising:
- identifying the hygiene device from a plurality of devices based on an identification of the hygiene device; and
- locking down wireless connection between the hygiene device and the mobile device in response to the hygiene device being identified to ensure completion of data transmission between the hygiene device and the mobile device.

16. A method for maintaining hygiene of a portable box configured to be carried by a user for transportation of deliverable items, the method comprising:
- conducting hygiene cycles each including spraying a hygiene agent in liquid form into the box using a portable hygiene device attached to the box;
- controlling the conduction of each hygiene cycle of the hygiene cycles automatically using a mobile device configured to be carried by a user of the box and to be communicatively coupled to the hygiene device, the mobile device configured to receive a hygiene cycle schedule from a network, to learn ordering and delivery status of the deliverable items, to initiate the each hygiene cycle according to all the hygiene cycle schedule and the learned ordering and delivery status, to automatically learn the user's workload, and to adjust the hygiene cycle schedule according to the learned user's workload;
- recording information related to performance of each hygiene cycle of the hygiene cycles using the hygiene device; and
- transmitting the recorded information from the hygiene device to the mobile device.

17. The method of claim 16, wherein conducting the hygiene cycles comprises spraying the hygiene agent into the box when the box is empty.

18. The method of claim 17, wherein spraying the hygiene agent comprises using a plurality of nozzles positioned and oriented within the box to produce a mist of the hygiene agent in the box.

19. The method of claim 17, further comprising allowing the user to initiate each hygiene cycle of the hygiene cycles using the mobile device.

20. The method of claim 19, further comprising:
- automatically timing a spray duration using the hygiene device, the spray duration being a time interval during which the hygiene agent is to be sprayed into the box; and
- allowing the user to manually stop the spray duration using the mobile device.

* * * * *

UNITED STATES PATENT AND TRADEMARK OFFICE
CERTIFICATE OF CORRECTION

PATENT NO. : 11,883,552 B2  
APPLICATION NO. : 16/349454  
DATED : January 30, 2024  
INVENTOR(S) : Wei et al.

Page 1 of 1

It is certified that error appears in the above-identified patent and that said Letters Patent is hereby corrected as shown below:

In the Claims

In Column 34, Line 43, in Claim 2, delete "box ." and insert --box.-- therefor

In Column 34, Line 51, in Claim 5, delete "informationom" and insert --information from-- therefor In Column 36, Line 14, in Claim 16, after "to", delete "all"

Signed and Sealed this  
Fourth Day of March, 2025

Coke Morgan Stewart  
*Acting Director of the United States Patent and Trademark Office*